(12) United States Patent
Oishi

(10) Patent No.: US 10,017,841 B2
(45) Date of Patent: Jul. 10, 2018

(54) COPPER ALLOY CASTING AND METHOD OF CASTING THE SAME

(75) Inventor: Keiichiro Oishi, Yao (JP)

(73) Assignee: MITSUBISHI SHINDOH CO., LTD., Tokyo (JP)

( * ) Notice: Subject to any disclaimer, the term of this patent is extended or adjusted under 35 U.S.C. 154(b) by 1674 days.

(21) Appl. No.: 11/573,640

(22) PCT Filed: Aug. 10, 2005

(86) PCT No.: PCT/JP2005/014698
§ 371 (c)(1),
(2), (4) Date: Feb. 12, 2007

(87) PCT Pub. No.: WO2006/016630
PCT Pub. Date: Feb. 16, 2006

(65) Prior Publication Data
US 2007/0158002 A1    Jul. 12, 2007

(30) Foreign Application Priority Data
Aug. 10, 2004    (JP) ................. 2004-233952

(51) Int. Cl.
*C22C 9/04*    (2006.01)
*B22D 21/02*    (2006.01)
(Continued)

(52) U.S. Cl.
CPC .............. *C22C 9/04* (2013.01); *B22D 21/022* (2013.01); *B22D 21/025* (2013.01); *B22D 27/00* (2013.01);
(Continued)

(58) Field of Classification Search
CPC .... B22D 21/022; B22D 21/025; B22D 27/00; C22C 9/00; C22C 9/04; C22F 1/08
(Continued)

(56) References Cited

U.S. PATENT DOCUMENTS

| 2,521,663 A | 9/1950 | Zunick |
| 3,676,083 A | 7/1972 | Cheney et al. |

(Continued)

FOREIGN PATENT DOCUMENTS

| EP | 1 681 360 A1 | 7/2006 |
| JP | 50-078519 | 6/1975 |

(Continued)

OTHER PUBLICATIONS

International Search Report issued in corresponding application No. PCT/JP2005/014697, completed Sep. 2, 2005 and dated Sep. 20, 2005.

(Continued)

*Primary Examiner* — Colleen P Dunn
*Assistant Examiner* — Nicholas A Wang
(74) *Attorney, Agent, or Firm* — Griffin and Szipl PC

(57) ABSTRACT

Copper alloy casting contains Cu: 58-72.5 mass %; Zr: 0.0008-0.045 mass %; P: 0.01-0.25 mass %; one or more elements selected from Pb: 0.01-4 mass %, Bi: 0.01-3 mass %, Se: 0.03-1 mass %, and Te: 0.05-1.2 mass %; and Zn: a remainder, wherein [Cu]−3[P]+0.5([Pb]+[Bi]+[Se]+[Te])= 60-90, [P]/[Zr]=0.5-120, and 0.05[γ]+([Pb]+[Bi]+[Se]+ [Te])= 0.45-4 (the content of an element 'a' is denoted as [a] mass %; the content of γ phase is denoted as [γ]% by area ratio; and an element 'a' that is not contained is denoted as [a]=0). The total content of α phase and γ phase is 85% or more, γ phase content is 25% or less by area ratio, and mean grain size in the macrostructure during melt-solidification is 250 μm or less.

30 Claims, 6 Drawing Sheets

(A)

(B)

(51) Int. Cl.
  *C22C 1/06* (2006.01)
  *C22C 30/02* (2006.01)
  *C22C 30/06* (2006.01)
  *C22F 1/08* (2006.01)
  *B22D 27/00* (2006.01)
  *C22C 1/03* (2006.01)
  *C22C 9/00* (2006.01)

(52) U.S. Cl.
  CPC .................. *C22C 1/03* (2013.01); *C22C 1/06* (2013.01); *C22C 9/00* (2013.01); *C22C 30/02* (2013.01); *C22C 30/06* (2013.01); *C22F 1/08* (2013.01)

(58) Field of Classification Search
  USPC .................................. 148/434; 420/472, 484
  See application file for complete search history.

(56) References Cited

U.S. PATENT DOCUMENTS

| | | | |
|---|---|---|---|
| 3,912,552 | A | 10/1975 | Schultz et al. |
| 3,928,028 | A | 12/1975 | Yarwood |
| 4,110,132 | A | 8/1978 | Parikh et al. |
| 4,238,249 | A * | 12/1980 | Ruchel .......................... 148/554 |
| 4,353,415 | A | 10/1982 | Klaschka et al. |
| 4,822,560 | A | 4/1989 | Oyama et al. |
| 5,370,840 | A | 12/1994 | Caron et al. |
| 5,871,861 | A | 2/1999 | Hirokou et al. |
| 6,401,323 | B1 | 6/2002 | Roller et al. |
| 6,413,330 | B1 | 7/2002 | Oishi |
| 6,627,011 | B2 | 9/2003 | Sugawara et al. |
| 2002/0006351 | A1 | 1/2002 | Sugawara et al. |
| 2004/0234412 | A1 | 11/2004 | Oishi et al. |
| 2005/0039827 | A1* | 2/2005 | Yamagishi et al. ........... 148/554 |
| 2006/0222557 | A1 | 10/2006 | Pike, Jr. |
| 2008/0073005 | A1 | 3/2008 | Buck |
| 2010/0297464 | A1 | 11/2010 | Oishi |

FOREIGN PATENT DOCUMENTS

| | | |
|---|---|---|
| JP | 52-107227 | 9/1977 |
| JP | 54-92516 | 7/1979 |
| JP | 55-070494 | 5/1980 |
| JP | 58-39900 | 9/1983 |
| JP | 61-000542 | 1/1986 |
| JP | 61-133357 A | 6/1986 |
| JP | 62-274036 | 11/1987 |
| JP | 62-297429 | 12/1987 |
| JP | 1-162737 | 6/1989 |
| JP | 3-291344 | 12/1991 |
| JP | 6-058688 | 3/1994 |
| JP | 6-184669 | 7/1994 |
| JP | 06-184674 A | 7/1994 |
| JP | 11-001736 | 1/1999 |
| JP | 11-1736 | 1/1999 |
| JP | 38-20467 | 2/1999 |
| JP | 11-58034 A | 3/1999 |
| JP | 2000-119775 A | 4/2000 |
| JP | 2000-199023 | 7/2000 |
| JP | 2001-247923 | 9/2001 |
| JP | 2004-100041 | 4/2004 |
| JP | 2004-100042 A | 4/2004 |
| JP | 2004-143541 | 5/2004 |
| JP | 2004-183056 A1 | 7/2004 |
| JP | 2004-233952 A | 8/2004 |
| WO | 94/10352 | 5/1994 |
| WO | 2004/022805 A1 | 3/2004 |

OTHER PUBLICATIONS

Restriction/Election issued in co-pending U.S. Appl. No. 11/573,632, dated Sep. 30, 2009.
Office Action issued in co-pending related U.S. Appl. No. 11/573,638, dated Jul. 6, 2010.
"Exhibit D" as filed in a corresponding related application (Binary Alloy Phase Diagrams, vol. 1, American Society for Metals, pp. 819-820, 971, 982 and 19).
"Exhibit A" (Metals Handbook Ninth Edition, vol. 9 Metallography and Microstructures, American Society for Metals, pp. 629-631).
"Exhibit C" p. E 41 of Glossary for Metalurgical Terms, The Japan Institute of Metals, 1995.
"Exhibit D" (ASM Metals Handbook 8th edition, vol. 8, Metallography, Structures and Phase Diagrams, 301 & D-2, American Society for Metals).
"Exhibit E" (Metals Handbook Ninth Edition, vol. 9, Metallography and Microstructures, American Society for Metals, pp. 641-642).
"Exhibit F" (the Metals Handbook 8th Edition, vol. 7, Atlas of Microstructures of Industrial Alloys, 290 & F-2, American Society for Metals).
"Exhibit H" (Metals Handbook 8th Edition, vol. 7, Atlas of Microstructures of Industrial Alloys, American Society for Metals, p. 286).
Cast Nonferous: Heat Treating of Copper and Copper Alloys, downloaded Nov. 2, 2010, from http://www.keytometals.com/Article25.htm, two pages.
Visual Acuity of the Human Eye, 3 pages, downloaded from http://www.ndt.ed.org/EductationResources/CommunityCollege/PenetrantTest/Introduction/visualacuity.htm.
V. Ryan, Annealing Metals, downloaded Nov. 2, 2010 from http://www.technologystudent.com/equip1/heat3.htm, 2 pages.
The Annual Book of ASTM Standards 2000, vol. 02.01, Section 2, p. 876.
Page 171 of Metals Handbook 8th Edition, vol. 8, Metallography, Structures and Phase Diagrams,1973.
Pages 641, 642 and 411 of Metals Handbook® Ninth Edition, vol. 9, Metallography and Microstructures, 1985.
Gubner, Rolf et al., Grain Boundary Corrosion of Copper Canister Weld Material, TR-06-01 (Svensk Kämbränslehantering AB 2006).
ASM Specialty Handbook: Copper and Copper Alloys, pp. 1-9 (ASM International 2001).
Procedures: Copper Welding, at http://www.brazing.com/techguide/procedures/copper_welding.asp (downloaded Jun. 13, 2012, six pages.
Metals Handbook® Ninth Edition, vol. 9, Metallography and Microstructures 155 and 408 (American Society for Metals 1985).
Pages 1, 3, 5, 15 and 16 of Terms and Definition of Metals Handbook 9th Edition, vol. 9, Metallography and Microstructures, American Society for Metals, filed in related U.S. Appl. No. 11/573,632 as Exhibit E, 1985.
Pages 257-259 of ASM Specialty Handbook, Copper and Copper Alloys, ASM International, filed in related U.S. Appl. No. 1/573,632 as Exhibit F, 1997.
English translation of JP2000-119775, 2000.
Office Actin issued in co-pending related U.S. Appl. No. 11/573,632 dated Aug. 22, 2011.
Metals Handbook 290 (8th Edition 1972), filed in related application as Exhibit C3.
ASM Specialty Handbook® Copper and Copper Alloys 243-246 (2001), filed in related application as Exhibit E3.
Materials Mechanical Size Effects: a Review, 23 Materials Technology 193-209 (2008), filed in related as Exhibit F3.
Exhibit A2, filed in a co-pending related applicaiton, which is a Metals Handbook 8th Ed., vol. 7, Atlas of Microstructures of Industrial Alloys 280 (American Society for Metals 1972).
Exhibit B2, filed in a co-pending related application, which is Metals Handbook 8th Ed., vol. 8, Metallography, Sturctures and Phase Diagrams 171 (American Society for Metals 1973).
Pages 277, 278, 365, 373, 374, 383, 384, 407 and 408 of Degarmo, E. Paul; Black, J T.; Kohser, Ronald A., Materials and Processed in Manufacturing 9th edition (2003), John Wiley & Sons, Inc., attached hereto as Exhibit J.
Pages 9 and 15 of Terms and Definition of Metals Handbook 9th Edition, vol. 9, Metallography and Microstructures, American Society For Metals, attached hereto as Exhibit I, 1985.
Restriction/Election dated Apr. 13, 2011 in co-pending related U.S. Appl. No. 11/573,638.

(56) References Cited

OTHER PUBLICATIONS

International Search Report issued in related application No. PCT/JP2005/018107, completed Dec. 13, 2005 and dated Dec. 20, 2005.
Office Action issued in co-pending related U.S. Appl. No. 12/088,822 dated Mar. 21, 2013.
E. Paul Degarmo, Materials and Processes in Manufacturing 276-295 (John Wiley & Sons, Inc. 9th Ed. 2003), filed in a related application as Exhibit A1.
"Casting and Solidification Process," dated Jan. 9, 2010, at http://classes.engr.oregonstate.edu/mime/winter2010/ie337-001/Laboratories/5.Solidification%20Lab.pdf, downloaded Nov. 23, 2011, three pages, filed in a related application as Exhibit B1.
E. Paul Degarmo, Materials and Processes in Manufacturing 82-85 (John Wiley & Sons, Inc. 9th Ed. 2003), filed in a related application as Exhibit C1.
Patent Abstracts of Japan English Abstract corresponding to JP 2000/119775, filed in a related application as Exhibit D1, 2000.
Final Office Action issued in co-pending related U.S. Appl. No. 10/596,849 dated Jun. 26, 2014.
Office Action issued in co-pending related U.S. Appl. No. 11/573,632 dated Feb. 4, 2015.
Restriction/Election issued in co-pending related U.S. Appl. No. 11/573,632 dated Mar. 21, 2014.
Handbook of Workability and Porcess Design, G.E. Dieter, H.A. Kuhn, and S.L. Semiatin, etditors, p. 35-44, DOI:101361/hwpd2003po35, Chapter 3, Evolution of Microstucture during Hot Working, ASM International, 2003. (obtained directly from the USPTO—no better quality version available).
Final Office Action issued co-pending U.S. Appl. No. 10/596,849 dated Jul. 2, 2015.

\* cited by examiner

FIG. 1
(A)
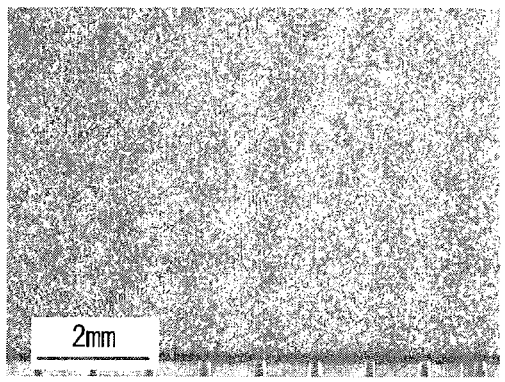
(B)
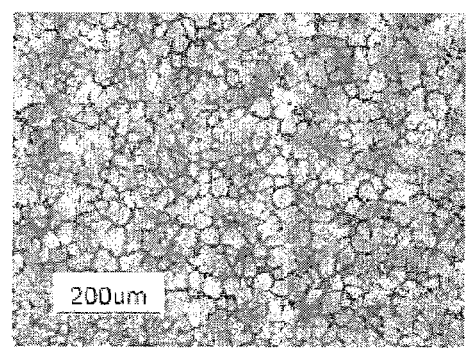
FIG. 2
(A)
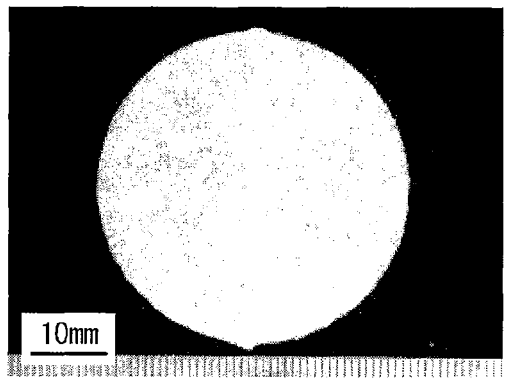
(B)
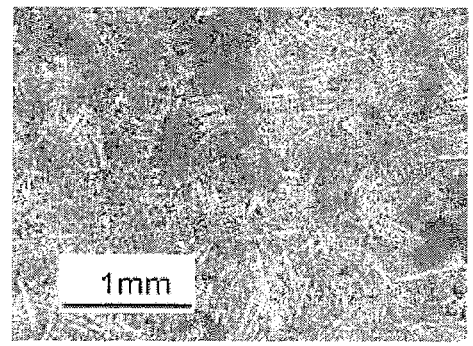

(A) (B) (C)

FIG. 7
(A)
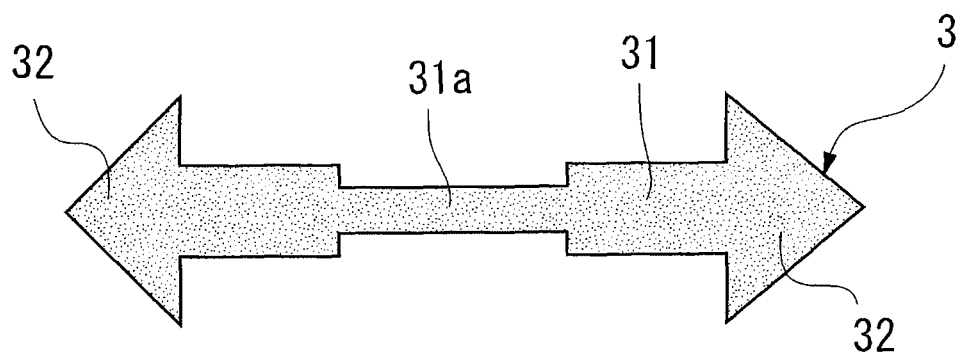
(B)
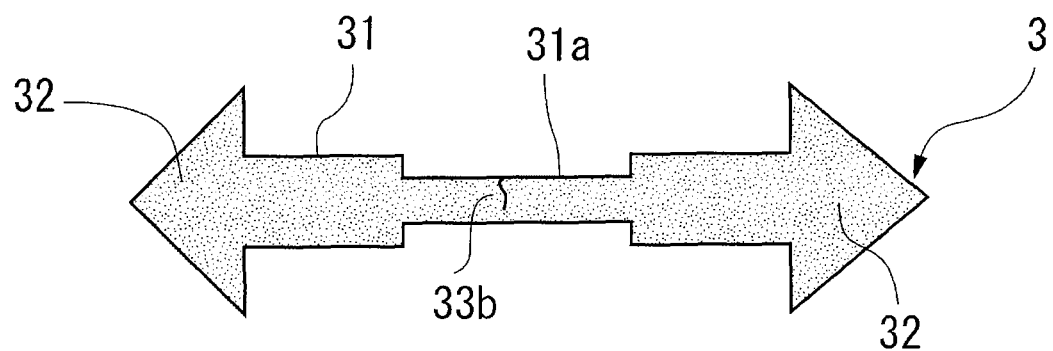
(C)
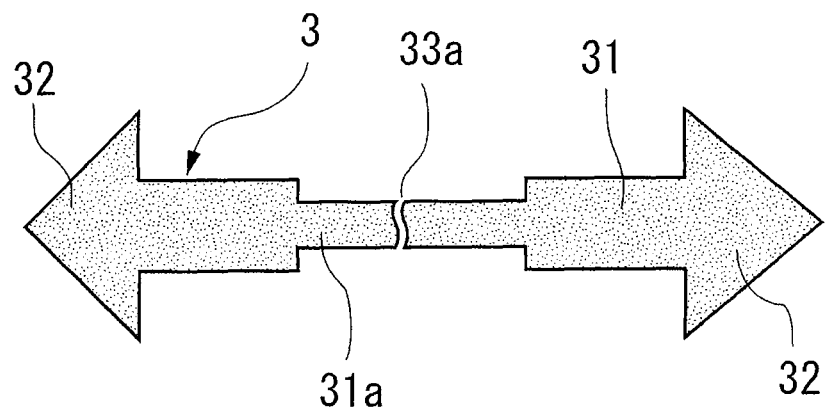

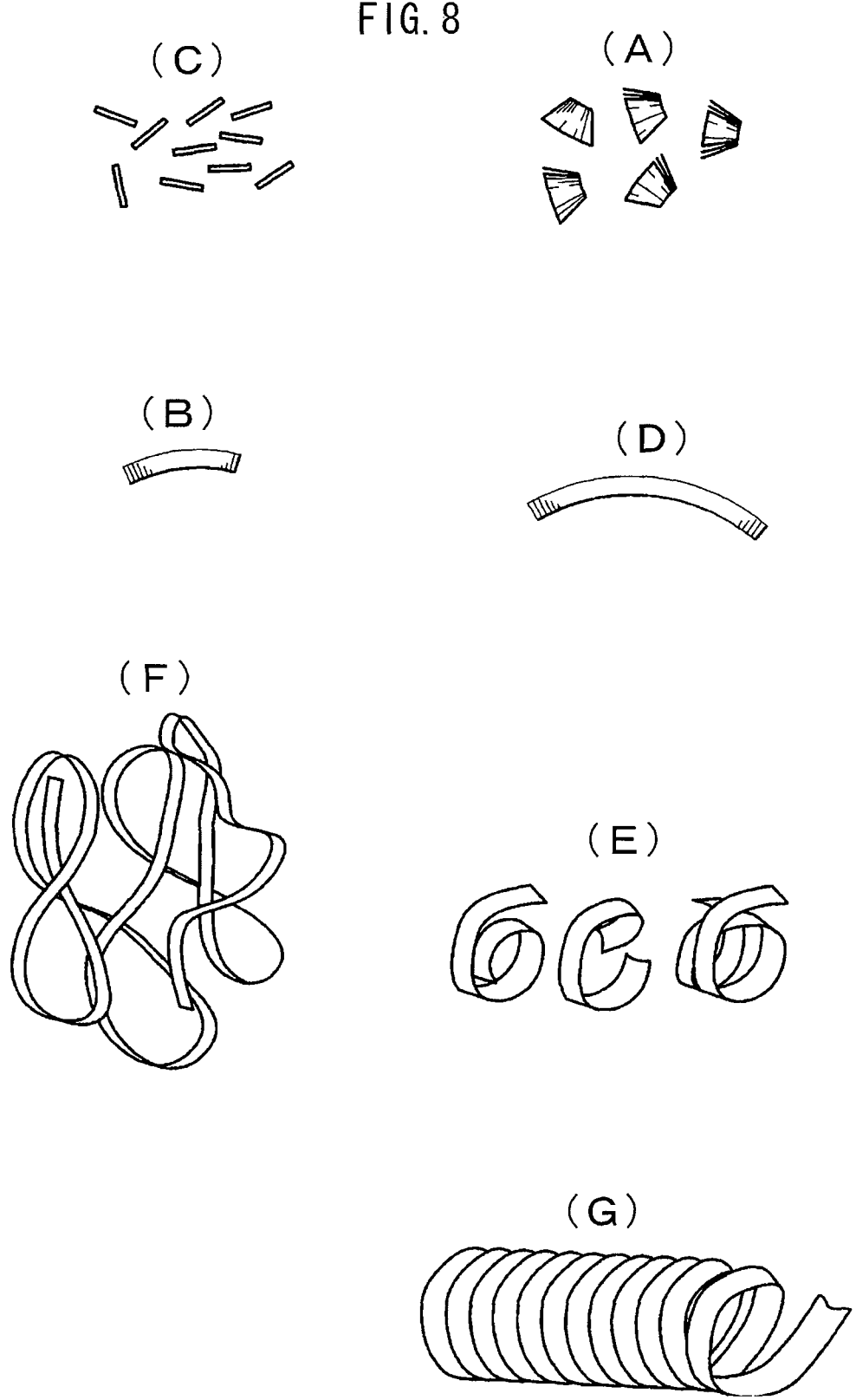

025# COPPER ALLOY CASTING AND METHOD OF CASTING THE SAME

This is a National Phase Application in the United States of International Patent Application No. PCT/JP2005/014698 filed Aug. 10, 2005, which claims priority on Japanese Patent Application No. 2004-233952, filed Aug. 10, 2004. The entire disclosures of the above patent applications are hereby incorporated by reference.

TECHNICAL FIELD

The present invention relates to a copper alloy casting, which has excellent machinability, strength, wear resistance and corrosion resistance and is preferably used as water contact metal fitting including water faucet of a water supply pipe, valves, cocks, joints, flanges, faucets, in-house built device, water discharging tools, joint clip, parts for boiler or the like which are used continuously or temporarily in contact with water (tap water or the like), friction engaging member including bearing, gear, cylinder, bearing retainer, impeller, parts for pumps, bearing or the like which makes a relative movement to a facing member (rotating shaft or the like) continuously or temporarily in contact with the facing member, or the structural material thereof, and a method of casting the same.

BACKGROUND ART

Generally, a copper alloy casting is used for a water contact metal fitting. For such a copper alloy casting fitting, it is ideal that a copper alloy having excellent machinability, strength, corrosion resistance, and castability be used as the structural material thereof.

In addition, bronze alloys such as CAC406 of JIS H5120 or the like are well known as a copper alloy having excellent machinability or the like.

However, the above alloys contain a large amount of Pb (4 mass % or more) to secure machinability. Pb is a harmful substance having a negative influence on human body and environment, therefore, in recent years, the usage of Pb has been strictly restricted. For example, when an operation in hot environment is performed such as melting, casting or the like of an alloy containing a large amount of Pb, the metallic vapor generated does harm to a human body and causes environmental contamination because such vapor comes to contain Pb. In addition, when an alloy containing a large amount of Pb is used for a water faucet, a valve or the like, Pb can be eluted due to the contact with potable water or the like.

Furthermore, the properties of the aforesaid bronze alloys such as strength, corrosion resistance, castability or the like are far from satisfactory.

Even in the related art, it is well known that grain refinement is extremely effective in improving the machinability, castability or the like of a copper alloy casting by removing dendrite structure, a typical structure of a casting.

Basically, the grains of a copper alloy are refined as follows: (A) the grains are refined during the melt-solidification of a copper alloy, or (B) the grains are refined by deforming such as rolling or the like, or by heating the melt-solidified copper alloy (ingot such as slab or the like; casting such as die casting or the like; molten casting products or the like), in which stacking energy such as distortion energy or the like acts as a driving force. In both cases, Zr is known as an element contributing to the grain refinement effectively.

In the case of method (A), since the grain refining effect of Zr during melt-solidification depends considerably upon the other elements and the contents thereof, the grains cannot be refined as much as desired. Consequently, method (B) is widely used, and the grains are refined by heating and then deforming a melt-solidified ingot, casting or the like.

JP-B-38-20467 discloses that the grains can be refined further as the content of Zr increases, on the basis of the measurement results that the mean grain size of a copper alloy containing Zr, P, and Ni, on which solution treatment and subsequent cold-working at the working rate of 75% are performed, is 280 µm when no Zr contained, 170 µm when 0.05 mass % of Zr contained, 50 µm when 0.13 mass % of Zr contained, 29 µm when 0.22 mass % of Zr contained, and 6 µm when 0.89 mass % of Zr contained. In addition, JP-B-38-20467 proposes that the content of Zr should be in the range of 0.05 to 0.3 mass % in order to avoid a negative influence caused by the excessive content of Zr.

Furthermore, JP-A-2004-100042 discloses that the mean grain size can be as fine as about 20 µm or less if a copper alloy, to which 0.15 to 0.5 mass % of Zr is added, is solution-treated and deformed after casting.

Patent Document 1: JP-B-38-20467
Patent Document 2: JP-A-2004-100042

However, if a casting is heated and deformed to refine the grains like method (B), the manufacturing cost rises. In addition, a deformation process for distortion is not always available depending on the shape of a casting. Therefore, it is preferable that the grains are refined while a copper alloy is being melt-solidified by method (A). However, as described earlier, in the case of method (A), since the grain-refining effect of Zr considerably depends on the other elements and the contents thereof during melt-solidification, the grains cannot be refined as much as expected even when the content of Zr increases. In addition, since Zr has an extremely strong affinity to oxygen, when Zr is melted and added in the air, Zr is likely to be oxidized, and thus the yield of Zr decreases drastically. As a result, even when an obtained casting contains a little amount of Zr, a considerable amount of Zr needs to be charged upon pouring. On the other hand, if too much oxide is generated during melting, the oxide can be included into a molten alloy during pouring, thereby inducing casting defects. In order to avoid the generation of the oxide, it can be considered that the raw materials are melted and cast under a vacuum or inert gas atmosphere; however, this method raises the manufacturing cost. Furthermore, since Zr is an expensive element, it is preferable that the adding amount of Zr be suppressed as low as possible from an economic viewpoint.

Consequently, it is demanded that the content of Zr be made as low as possible and a copper alloy casting, the grains of which are refined at the stage of melt-solidification during casting, be developed.

DISCLOSURE OF THE INVENTION

The invention has been finalized in views of the drawbacks inherent to the copper alloy castings in the related art, and it is an advantage of the invention to provide a copper alloy casting that has grains capable of being refined and satisfactory machinability even when the amount of Pb, harmful to a human body, is not large, and that can be used preferably as a water contact metal fitting, the structural material thereof or the like owing to various excellent properties such as strength, ductility, corrosion resistance, castability or the like. It is also an advantage of the invention to provide a method of casting capable of preferably manufacturing the above copper alloy casting.

The invention proposes the following copper alloy castings and the methods of casting the same in order to achieve the above advantages.

That is, the invention proposes, firstly, a copper alloy casting (hereinafter referred to as 'first copper alloy casting') containing Cu: 58 to 72.5 mass % (preferably 60 to 72.5 mass %, more preferably 60.5 to 70 mass %, and optimally 61.5 to 66 mass %); Zr: 0.0008 to 0.045 mass % (preferably 0.003 to 0.029 mass %, more preferably 0.005 to 0.024 mass %, and optimally 0.007 to 0.019 mass %); P: 0.01 to 0.25 mass % (preferably 0.02 to 0.18 mass %, more preferably 0.03 to 0.15 mass %, and optimally 0.035 to 0.12 mass %); one or more elements selected from Pb: 0.01 to 4 mass % (preferably 0.05 to 2.5 mass %, more preferably 0.45 to 1.5 mass %, and optimally 0.45 to 1 mass %), Bi: 0.01 to 3 mass % (preferably 0.05 to 2 mass %, more preferably 0.45 to 1.5 mass %, and optimally 0.45 to 1 mass %), Se: 0.03 to 1 mass % (preferably 0.05 to 0.5 mass %, and more preferably 0.05 to 0.3 mass %), and Te: 0.05 to 1.2 mass % (preferably 0.1 to 0.8 mass %, and more preferably 0.2 to 0.7 mass %); and Zn: the remainder and satisfying the following conditions (1) to (5). It is preferable that the first copper alloy casting further satisfy the following conditions (9) to (14) in addition to the above conditions.

The invention proposes, secondly, a copper alloy casting (hereinafter referred to as 'second copper alloy casting') further containing Sn and/or Al in addition to the composition of the first copper alloy casting, that is, containing Cu: 58 to 72.5 mass % (preferably 60 to 72.5 mass %, more preferably 60.5 to 70 mass %, and optimally 61.5 to 66 mass %); Zr: 0.0008 to 0.045 mass % (preferably 0.003 to 0.029 mass %, more preferably 0.005 to 0.024 mass %, and optimally 0.007 to 0.019 mass %); P: 0.01 to 0.25 mass % (preferably 0.02 to 0.18 mass %, more preferably 0.03 to 0.15 mass %, and optimally 0.035 to 0.12 mass %); one or more elements selected from Pb: 0.01 to 4 mass % (preferably 0.05 to 2.5 mass %, more preferably 0.45 to 1.5 mass %, and optimally 0.45 to 1 mass %), Bi: 0.01 to 3 mass % (preferably 0.05 to 2 mass %, more preferably 0.45 to 1.5 mass %, and optimally 0.45 to 1 mass %), Se: 0.03 to 1 mass % (preferably 0.05 to 0.5 mass %, and more preferably 0.05 to 0.3 mass %), and Te: 0.05 to 1.2 mass % (preferably 0.1 to 0.8 mass %, and more preferably 0.2 to 0.7 mass %); Sn: 0.05 to 4 mass % (preferably 0.2 to 3.5 mass %, more preferably 0.5 to 3 mass %, and optimally 0.7 to 2.5 mass %) and/or Al: 0.01 to 4 mass % (preferably 0.03 to 2.5 mass %, more preferably 0.05 to 1.5 mass %, and optimally 0.1 to 0.5 mass %); and Zn: the remainder and satisfying the following conditions (1) to (8). It is preferable that the second copper alloy casting further satisfy the following conditions (9) to (14) in addition to the above conditions.

The invention proposes, thirdly, a copper alloy casting (hereinafter referred to as 'third copper alloy casting') further containing As and/or Sb in addition to the composition of the first copper alloy casting, that is, containing Cu: 58 to 72.5 mass % (preferably 60 to 72.5 mass %, more preferably 60.5 to 70 mass %, and optimally 61.5 to 66 mass %); Zr: 0.0008 to 0.045 mass % (preferably 0.003 to 0.029 mass %, more preferably 0.005 to 0.024 mass %, and optimally 0.007 to 0.019 mass %); P: 0.01 to 0.25 mass % (preferably 0.02 to 0.18 mass %, more preferably 0.03 to 0.15 mass %, and optimally 0.035 to 0.12 mass %); one or more elements selected from Pb: 0.01 to 4 mass % (preferably 0.05 to 2.5 mass %, more preferably 0.45 to 1.5 mass %, and optimally 0.45 to 1 mass %), Bi: 0.01 to 3 mass % (preferably 0.05 to 2 mass %, more preferably 0.45 to 1.5 mass %, and optimally 0.45 to 1 mass %), Se: 0.03 to 1 mass % (preferably 0.05 to 0.5 mass %, and more preferably 0.05 to 0.3 mass %), and Te: 0.05 to 1.2 mass % (preferably 0.1 to 0.8 mass %, and more preferably 0.2 to 0.7 mass %); As: 0.02 to 0.2 mass % (preferably 0.03 to 0.12 mass %) and/or Sb: 0.02 to 0.2 mass % (preferably: 0.03 to 0.12 mass %); and Zn: the remainder and satisfying the following conditions (1) to (5). It is preferable that the third copper alloy casting further satisfy the following conditions (9) to (14) in addition to the above conditions.

The invention proposes, fourthly, a copper alloy casting (hereinafter referred to as 'fourth copper alloy casting') further containing one or more element selected from Mn, Si and Mg in addition to the composition of the first copper alloy casting, that is, containing Cu: 58 to 72.5 mass % (preferably 60 to 72.5 mass %, more preferably 60.5 to 70 mass %, and optimally 61.5 to 66 mass %); Zr: 0.0008 to 0.045 mass % (preferably 0.003 to 0.029 mass %, more preferably 0.005 to 0.024 mass %, and optimally 0.007 to 0.019 mass %); P: 0.01 to 0.25 mass % (preferably 0.02 to 0.18 mass %, more preferably 0.03 to 0.15 mass %, and optimally 0.035 to 0.12 mass %); one or more elements selected from Pb: 0.01 to 4 mass % (preferably 0.05 to 2.5 mass %, more preferably 0.45 to 1.5 mass %, and optimally 0.45 to 1 mass %), Bi: 0.01 to 3 mass % (preferably 0.05 to 2 mass %, more preferably 0.45 to 1.5 mass %, and optimally 0.45 to 1 mass %), Se: 0.03 to 1 mass % (preferably 0.05 to 0.5 mass %, and more preferably 0.05 to 0.3 mass %), and Te: 0.05 to 1.2 mass % (preferably 0.1 to 0.8 mass %, and more preferably 0.2 to 0.7 mass %); one or more elements selected from Mn: 0.1 to 5 mass % (preferably 0.5 to 4.5 mass %, and more preferably 1 to 3.5 mass %), Si: 0.05 to 2 mass % (preferably 0.2 to 1.5 mass %), and Mg: 0.001 to 0.2 mass % (preferably 0.002 to 0.15 mass %, and more preferably 0.005 to 0.1 mass %); and Zn: the remainder and satisfying the following conditions (1) to (5). It is preferable that the fourth copper alloy casting further satisfy the following conditions (9) to (14) in addition to the above conditions.

The invention proposes, fifthly, a copper alloy casting (hereinafter referred to as 'fifth copper alloy casting') further containing Sn and/or Al, and As and/or Sb in addition to the composition of the first copper alloy casting, that is, containing Cu: 58 to 72.5 mass % (preferably 60 to 72.5 mass %, more preferably 60.5 to 70 mass %, and optimally 61.5 to 66 mass %); Zr: 0.0008 to 0.045 mass % (preferably 0.003 to 0.029 mass %, more preferably 0.005 to 0.024 mass %, and optimally 0.007 to 0.019 mass %); P: 0.01 to 0.25 mass % (preferably 0.02 to 0.18 mass %, more preferably 0.03 to 0.15 mass %, and optimally 0.035 to 0.12 mass %); one or more elements selected from Pb: 0.01 to 4 mass % (preferably 0.05 to 2.5 mass %, more preferably 0.45 to 1.5 mass %, and optimally 0.45 to 1 mass %), Bi: 0.01 to 3 mass % (preferably 0.05 to 2 mass %, more preferably 0.45 to 1.5 mass %, and optimally 0.45 to 1 mass %), Se: 0.03 to 1 mass % (preferably 0.05 to 0.5 mass %, and more preferably 0.05 to 0.3 mass %), and Te: 0.05 to 1.2 mass % (preferably 0.1 to 0.8 mass %, and more preferably 0.2 to 0.7 mass %); Sn: 0.05 to 4 mass % (preferably 0.2 to 3.5 mass %, more preferably 0.5 to 3 mass %, and optimally 0.7 to 2.5 mass %) and/or Al: 0.01 to 4 mass % (preferably 0.03 to 2.5 mass %, more preferably 0.05 to 1.5 mass %, and optimally 0.1 to 0.5 mass %); As: 0.02 to 0.2 mass % (preferably 0.03 to 0.12 mass %) and/or Sb: 0.02 to 0.2 mass % (preferably: 0.03 to 0.12 mass %); and Zn: the remainder and satisfying the following conditions (1) to (8). It is preferable that the fifth copper alloy casting further satisfy the following conditions (9) to (14) in addition to the above conditions.

The invention proposes, sixthly, a copper alloy casting (hereinafter referred to as 'sixth copper alloy casting') further containing Sn and/or Al and one or more element selected from Mn, Si and Mg in addition to the composition of the first copper alloy casting, that is, containing Cu: 58 to 72.5 mass % (preferably 60 to 72.5 mass %, more preferably 60.5 to 70 mass %, and optimally 61.5 to 66 mass %); Zr: 0.0008 to 0.045 mass % (preferably 0.003 to 0.029 mass %, more preferably 0.005 to 0.024 mass %, and optimally 0.007 to 0.019 mass %); P: 0.01 to 0.25 mass % (preferably 0.02 to 0.18 mass %, more preferably 0.03 to 0.15 mass %, and optimally 0.035 to 0.12 mass %); one or more elements selected from Pb: 0.01 to 4 mass % (preferably 0.05 to 2.5 mass %, more preferably 0.45 to 1.5 mass %, and optimally 0.45 to 1 mass %), Bi: 0.01 to 3 mass % (preferably 0.05 to 2 mass %, more preferably 0.45 to 1.5 mass %, and optimally 0.45 to 1 mass %), Se: 0.03 to 1 mass % (preferably 0.05 to 0.5 mass %, and more preferably 0.05 to 0.3 mass %), and Te: 0.05 to 1.2 mass % (preferably 0.1 to 0.8 mass %, and more preferably 0.2 to 0.7 mass %); Sn: 0.05 to 4 mass % (preferably 0.2 to 3.5 mass %, more preferably 0.5 to 3 mass %, and optimally 0.7 to 2.5 mass %) and/or Al: 0.01 to 4 mass % (preferably 0.03 to 2.5 mass %, more preferably 0.05 to 1.5 mass %, and optimally 0.1 to 0.5 mass %); one or more elements selected from Mn: 0.1 to 5 mass % (preferably 0.5 to 4.5 mass %, and more preferably 1 to 3.5 mass %), Si: 0.05 to 2 mass % (preferably 0.2 to 1.5 mass %), and Mg: 0.001 to 0.2 mass % (preferably 0.002 to 0.15 mass %, and more preferably 0.005 to 0.1 mass %); and Zn: the remainder and satisfying the following conditions (1) to (8). It is preferable that the sixth copper alloy casting further satisfy the following conditions (9) to (14) in addition to the above conditions.

The invention proposes, seventhly, a copper alloy casting (hereinafter referred to as 'seventh copper alloy casting') further containing As and/or Sb and one or more element selected from Mn, Si and Mg in addition to the composition of the first copper alloy casting, that is, containing Cu: 58 to 72.5 mass % (preferably 60 to 72.5 mass %, more preferably 60.5 to 70 mass %, and optimally 61.5 to 66 mass %); Zr: 0.0008 to 0.045 mass % (preferably 0.003 to 0.029 mass %, more preferably 0.005 to 0.024 mass %, and optimally 0.007 to 0.019 mass %); P: 0.01 to 0.25 mass % (preferably 0.02 to 0.18 mass %, more preferably 0.03 to 0.15 mass %, and optimally 0.035 to 0.12 mass %); one or more elements selected from Pb: 0.01 to 4 mass % (preferably 0.05 to 2.5 mass %, more preferably 0.45 to 1.5 mass %, and optimally 0.45 to 1 mass %), Bi: 0.01 to 3 mass % (preferably 0.05 to 2 mass %, more preferably 0.45 to 1.5 mass %, and optimally 0.45 to 1 mass %), Se: 0.03 to 1 mass % (preferably 0.05 to 0.5 mass %, and more preferably 0.05 to 0.3 mass %), and Te: 0.05 to 1.2 mass % (preferably 0.1 to 0.8 mass %, and more preferably 0.2 to 0.7 mass %); As: 0.02 to 0.2 mass % (preferably 0.03 to 0.12 mass %) and/or Sb: 0.02 to 0.2 mass % (preferably: 0.03 to 0.12 mass %); one or more elements selected from Mn: 0.1 to 5 mass % (preferably 0.5 to 4.5 mass %, and more preferably 1 to 3.5 mass %), Si: 0.05 to 2 mass % (preferably 0.2 to 1.5 mass %), and Mg: 0.001 to 0.2 mass % (preferably 0.002 to 0.15 mass %, and more preferably 0.005 to 0.1 mass %); and Zn: the remainder and satisfying the following conditions (1) to (5). It is preferable that the seventh copper alloy casting further satisfy the following conditions (9) to (14) in addition to the above conditions.

The invention proposes, eighthly, a copper alloy casting (hereinafter referred to as 'eighth copper alloy casting') further containing Sn and/or Al, As and/or Sb, and one or more element selected from Mn, Si and Mg in addition to the composition of the first copper alloy casting, that is, containing Cu: 58 to 72.5 mass % (preferably 60 to 72.5 mass %, more preferably 60.5 to 70 mass %, and optimally 61.5 to 66 mass %); Zr: 0.0008 to 0.045 mass % (preferably 0.003 to 0.029 mass %, more preferably 0.005 to 0.024 mass %, and optimally 0.007 to 0.019 mass %); P: 0.01 to 0.25 mass % (preferably 0.02 to 0.18 mass %, more preferably 0.03 to 0.15 mass %, and optimally 0.035 to 0.12 mass %); one or more elements selected from Pb: 0.01 to 4 mass % (preferably 0.05 to 2.5 mass %, more preferably 0.45 to 1.5 mass %, and optimally 0.45 to 1 mass %), Bi: 0.01 to 3 mass % (preferably 0.05 to 2 mass %, more preferably 0.45 to 1.5 mass %, and optimally 0.45 to 1 mass %), Se: 0.03 to 1 mass % (preferably 0.05 to 0.5 mass %, and more preferably 0.05 to 0.3 mass %), and Te: 0.05 to 1.2 mass % (preferably 0.1 to 0.8 mass %, and more preferably 0.2 to 0.7 mass %); Sn: 0.05 to 4 mass % (preferably 0.2 to 3.5 mass %, more preferably 0.5 to 3 mass %, and optimally 0.7 to 2.5 mass %) and/or Al: 0.01 to 4 mass % (preferably 0.03 to 2.5 mass %, more preferably 0.05 to 1.5 mass %, and optimally 0.1 to 0.5 mass %); As: 0.02 to 0.2 mass % (preferably 0.03 to 0.12 mass %) and/or Sb: 0.02 to 0.2 mass % (preferably: 0.03 to 0.12 mass %); one or more elements selected from Mn: 0.1 to 5 mass % (preferably 0.5 to 4.5 mass %, and more preferably 1 to 3.5 mass %), Si: 0.05 to 2 mass % (preferably 0.2 to 1.5 mass %), and Mg: 0.001 to 0.2 mass % (preferably 0.002 to 0.15 mass %, and more preferably 0.005 to 0.1 mass %); and Zn: the remainder and satisfying the following conditions (1) to (8). It is preferable that the eighth copper alloy casting further satisfy the following conditions (9) to (14) in addition to the above conditions.

Meanwhile, in the following description, [a] indicates the content value of an element 'a', and the content of the element 'a' is expressed as [a] mass %. For example, the content of Cu is expressed as [Cu] mass %. In addition, the content of each phase is an area ratio, and, particularly, the content (surface area ratio) of γ-phase is expressed as [γ]%. The area ratio of each phase is measured by image analysis, specifically, by expressing the structure of a copper alloy casting, 200 times magnified by an optical microscope, in the binary system with an image processing software 'WinROOF' (manufactured by Tech-Jam Co., Ltd.), the area ratio is the average value of the area ratios measured in three different locations.

(1) $f1=[Cu]-3[P]+0.5\ ([Pb]+[Bi]+[Se]+[Te])-0.5[Sn]-1.8[Al]-([As]+[Sb])+[Mn]-3.5[Si]-0.5[Mg]=60$ to 90 (preferably $f1=61$ to 72, more preferably $f1=61.5$ to 68, and optimally $f1=62$ to 67). Meanwhile, in the above equation, an element 'a' that is not contained is expressed as $[a]=0$.

(2) $f2=[P]/[Zr]=0.5$ to 120 (preferably $f2=1$ to 30, more preferably $f2=1.4$ to 16, and optimally $f2=2$ to 12). Meanwhile, the method of measuring the area ratio of γ-phase will be described later.

(3) $f3=0.05[γ]+([Pb]+[Bi]+[Se]+[Te])=0.45$ to 4 (preferably $f3=0.6$ to 2, and more preferably $f3=0.95$ to 1.5). Meanwhile, an element 'a' that is not contained is expressed as $[a]=0$.

(4) The total content of α phase and γ phases should be 85% or more (preferably 90% or more, more preferably 95% or more, and optimally 98% or more), and the content of γ phase should be 25% or less (preferably 15% or less, and more preferably 0.1 to 10%).

(5) The mean grain size in the macrostructure should be 250 µm or less (preferably 100 µm or less, and more preferably 60 µm or less in the microstructure) at melt-solidification. In this case, the mean grain size in the macrostructure (or microstructure) at melt-solidification means the average value of the grain sizes in the macrostructure (or microstructure) of a casting (including various conventional casting methods such as permanent mold casting, sand casting, horizontal continuous casting, upward (upcast), semi-solid metal casting, semi-solid metal forging, molten alloy forging or the like), welding or fusing, on which no deformation process (extrusion, rolling or the like) or heating treatment is performed after melt-solidification. Meanwhile, in the present description, a 'casting' means a product, all or part of which is melted and solidified, and includes casting such as ingot, slab and billet for rolling or extrusion as well as sand casting, permanent mold casting, low-pressure casting, die casting, lost wax, semi-solid metal molding, semi-solid casting (for example, thixo-casting, rheo-casting), squeeze, centrifugal casting, continuous casting (for example, rod, hollow rod, irregular-shaped rod, irregular-shaped hollow rod, coil material, wire or the like manufactured by horizontal continuous casting, upward, upcast), casting manufactured by molten alloy forging (direct forging), thermal spraying, build-up, lining, overlay. In addition, welding is also included in the casting family in the broad sense of the term, since the mother material is partially melted and solidified before being welded.

(6) f4=[Zn]+2.5[Sn]+3[Al]=15 to 42 (preferably f4=20 to 41, more preferably f4=25 to 40, and optimally f4=30 to 39). Meanwhile, an element 'a' that is not contained is expressed as [a]=0.

(7) f5=([Zn]+2.5[Sn]+3[Al])/[Zr]=500 to 20000 (preferably f5=800 to 10000, more preferably f5=1200 to 6000, and optimally f5=1600 to 4500). Meanwhile, an element 'a' that is not contained is expressed as [a]=0.

(8) f6=([Zn]+2.5[Sn]+3[Al])/[P]=75 to 3000 (preferably f6=150 to 1600, more preferably f6=200 to 1200, and optimally f6=250 to 1000). Meanwhile, an element 'a' that is not contained is expressed as [a]=0.

(9) The primary crystal that appears during melt-solidification is α-phase.

(10) During melt-solidification, peritectic reaction occurs.

(11) During melt-solidification, a crystal structure, in which dendrite network is divided, is formed.

(12) The two-dimensional shape of the grains during melt-solidification is circular, substantially circular, oval, cross-like, acicular, or polygonal.

(13) α phase should be divided finely in the matrix, and γ phase or high Sn-concentrated part generated by segregation is distributed uniformly in the matrix.

(14) When Pb or Bi is contained, particles of Pb or Bi are uniform in diameter and are distributed uniformly in the matrix.

In the first to eighth copper alloy casting, Cu is a main element of the copper alloy composing the casting, and the content of Cu needs to be 58 mass % or more in order to secure the corrosion resistance (dezincification corrosion resistance, stress corrosion cracking resistance) and mechanical properties required for an industrial material. However, if the content of Cu exceeds 72.5 mass %, the strength and corrosion resistance deteriorate, and the effect of co-addition of Zr and P on grain refinement, as described below, is possibly impaired. Considering the above facts, the content of Cu needs to be in the range of 58 to 72.5 mass %, preferably 60 to 72.5 mass %, more preferably 60.5 to 70 mass %, and optimally 61.5 to 66 mass %. In addition, in order to refine the grains, it is required to consider the relationship between Cu and the other elements and to satisfy the condition (1). That is, the contents of Cu and the other elements need to satisfy the formula f1 ([Cu]−3[P]+0.5([Pb]+[Bi]+[Se]+[Te])−0.5[Sn]−1.8[Al]−([As]+[Sb])+[Mn]−3.5[Si]−0.5[Mg])=60 to 90, preferably f1=61 to 72, more preferably f1=61.5 to 68, and optimally f1=62 to 67.

In the first to eighth copper alloy casting, Zn, Like Cu, is also a main element of the copper alloy composing the casting. Zn decreases the stacking fault energy of the alloy; generates peritectic reaction; contributes to the grain refinement of the casting, improves flowability of the molten alloy, lowers melting temperature, prevents Zr loss by oxidation, improves corrosion resistance and machinability, and improves the mechanical strength such as tensile strength, proof stress, impact strength, fatigue strength or the like. Considering the above facts, the content of Zn is to be the remaining balance after the deduction of total content of each alloying element.

In the first to eighth copper alloy casting, Zr and P are added together in order to refine the grains of the copper alloy, particularly, to refine the grains during melt-solidification. That is, a single addition of either Zr or P can refine the grains of the copper alloy only slightly, same as the other additive elements. However, if Zr and P are added together, the grains of the copper alloy can be refined very effectively.

The grains are refined when the content of Zr is 0.0008 mass % or more, remarkably when the content of Zr is 0.003 mass % or more, more remarkably when the content of Zr is 0.005 mass % or more, and extremely remarkably when the content of Zr is 0.007 mass % or more. With respect to P, the grains are refined when the content of P is 0.01 mass %, remarkably when the content of P is 0.02 mass % or more, more remarkably when the content of P is 0.03 mass % or more, and extremely remarkably when the content of P is 0.035 mass %.

Meanwhile, if the adding amount of Zr reaches 0.045 mass %, and the adding amount of P reaches 0.25 mass %, the effect of the co-addition of Zr and P to refine the grains completely saturates regardless of the types and contents of the other component elements. Therefore, the adding amount of Zr and P required to refine the grains effectively is 0.045 mass % or less for Zr and 0.25 mass % or less for P. Meanwhile, if the adding amounts of Zr and P are as small as in the above ranges, the properties of the alloy obtained by the other component elements are not impaired. Rather, high Sn-concentrated part generated by segregation can be distributed uniformly in the matrix due to the grain refinement, instead of being concentrated at a certain location. At the same time, it is possible to make the molten alloy in a state where machinability-improving elements such as Pb, Bi or the like, which are not subject to solid solution, can be taken most advantage of. That is; where the particles are fine and uniform in diameter, and distributed and dispersed uniformly in the matrix. As a result, casting cracking can be prevented, and a robust casting with little amount of porosity, shrinkage cavity, blowhole, and microporosity can be obtained. In addition, the workability of cold drawing performed after casting can be improved, and the properties of the alloy can be further improved.

Meanwhile, since Zr has an extremely strong affinity to oxygen, when Zr is melted in the air or a scrap material is used as raw material, Zr is likely to form oxide or sulfide. Therefore, if Zr is added excessively, the viscosity of the molten alloy increases; casting defects are caused by the inclusion or the like of the oxide and sulfide; and blowhole or microporosity is highly likely to occur. In order to avoid the above trouble, it can be considered that Zr is melted and cast under the vacuum or completely inert gas atmosphere. However, such method cannot be widely used and thus the manufacturing cost of a copper alloy, to which Zr is added only for the purpose of grain refinement, drastically rises. Considering the above facts, the content of Zr, not in the form of oxide or sulfide, is preferably 0.029 mass % or less, more preferably 0.024 mass % or less, and optimally 0.019 mass % or less. In addition, if the amount of Zr is in the above ranges, the oxide or sulfide of Zr is less generated even when the casting is melted in the air as a recycled material. Therefore, a robust first to eighth copper alloy casting composed of fine crystal grains can be obtained again.

From the above facts, it is taken into account that a small amount of Zr should be added from an industrial viewpoint. The amount of Zr, therefore, needs to be in the range of 0.0008 to 0.045 mass %, preferably 0.003 to 0.029 mass %, more preferably 0.005 to 0.024 mass %, and optimally 0.007 to 0.019 mass %.

In addition, even though P is added with Zr to refine the grains as described above, P also has an influence on the corrosion resistance, castability or the like. Therefore, considering that the minimum value of the adding amount range of P has an influence on the corrosion resistance and castability as well as the grain refining function induced by the co-addition with Zr, and the maximum value of the adding amount of P has an influence on the ductility or the like, the adding amount of P needs to be in the range of 0.01 to 0.25 mass %, preferably 0.02 to 0.18 mass %, more preferably 0.03 to 0.15 mass %, and optimally 0.035 to 0.12 mass %.

In addition, in order for the co-addition of Zr and P to show the grain refining effect, it is also required that the contents of Zr and P satisfy the condition (2) as well as the contents of Zr and P determined in the aforesaid ranges. The grains are refined when the nucleation rate of the $\alpha$-phase primary crystal, which is crystallized from the molten liquid, is much faster than the grain growth rate of the dendrite crystal. In order to induce such phenomenon, it is required not only to determine the contents of Zr and P individually, but also to consider the co-addition ratio of Zr and P (f2=[P]/[Zr]). If each content of Zr and P is determined in a proper range so as to have a proper co-addition ratio, the co-addition and mutual action of Zr and P can remarkably facilitate the nucleation of the $\alpha$ phase primary crystal, and, consequently, the nucleation rate of the $\alpha$ phase becomes much faster than that of the grain growth of the dendrite crystal. When the contents of Zr and P are in the proper ranges and the co-adding ratio of Zr and P ([P]/[Zr]) is stoichiometric, an intermetallic compound of Zr and P (for example, ZrP, $ZrP_{1-x}$) can be generated in the $\alpha$ phase crystals by adding about several tens ppm of Zr, and the nucleation rate of the $\alpha$ phase is increased when the value of f2[P]/[Zr] is in the range of 0.5 to 120; remarkably in the range of 1 to 30; more remarkably in the range of 1.4 to 16; and further more remarkably in the range of 2 to 12. That is, f2, the co-addition ratio of Zr and P is an important factor for grain refinement, and if f2 is in the aforesaid range, the nucleation rate becomes much faster than the grain growth rate during melt-solidification.

In addition, as melt-solidification proceeds and the ratio of solid phase increases, grains begin to grow frequently and combine with each other in some parts. It is usually the case that $\alpha$ phase grains become larger. In this case, if peritectic reaction occurs while a molten alloy is being solidified, the molten alloy that is not yet solidified reacts with solid $\alpha$ phase by solid-liquid reaction and therefore, $\beta$ phase is generated while the $\alpha$ phase diminishes. As a result, the $\alpha$ phase is surrounded by the $\beta$ phase; the grain size of the $\alpha$ phase grain decreases; and the shape of the $\alpha$ phase grain becomes oval with the corners rounded off. If the solid phase becomes fine and oval, gas can be removed easily; the casting obtained has a resistance to cracking accompanied by solidification shrinkage caused while the molten alloy is solidified; shrinkage proceeds smoothly; various properties such as strength, corrosion resistance or the like at room temperature are improved. It is needless to say that, if the solid phase is fine and oval, the molten alloy has good flowability and becomes optimal for semi-solid metal solidifying method. In addition, if the fine and oval solid phase and liquid remain in the molten alloy at the final stage of solidification, the molten alloy can be sufficiently supplied to every corner of a mold, even if it has a complicated shape. Therefore, an excellently shaped casting, that is, a near net shape casting, can be manufactured. Meanwhile, unlike the equilibrium state, the peritectic reaction occurs within a wider composition range than that of the equilibrium state in a practical sense. In this case, equations f1 and f4 play important roles, and the maximum value of f1 (the minimum value of f4) is related mainly with the grain size after melt-solidification and the criterion that determines whether the peritectic reaction occurs or not. The minimum value of f1 (the maximum value of f4) is related mainly with the crystal size after melt-solidification and the threshold value that determines whether the primary crystal is $\alpha$ phase or not. As the values obtained from f1 and f4 are changed from the above-described preferable range to optimal range via more preferable range, the amount of the $\alpha$ phase primary crystal increases; the peritectic reaction generated at a non-equilibrium reaction is generated more actively; and, consequently, the grains obtained at room temperature become finer. Since f5 and f6 express the relationship between Zr and f4, and P and f4 respectively, it is also needless to say that f5 and f6 are important factors.

The above series of melt-solidification phenomena depend on the cooling rate. That is, in the rapid cooling performed at the cooling rate of $10^{5\circ}$ C./second or faster, the grains are not refined since there is no time for nucleation. In the slow cooling performed at the cooling rate of $10^{-3\circ}$ C./second or slower, the grains are not refined either since the grain growth or combination of grains is facilitated. Furthermore, as approaching the equilibrium, the composition range, in which peritectic reaction occurs, narrows. It is preferable that the cooling rate at the melt-solidification stage be in the range of $10^{-2}$ to $10^{4\circ}$ C./second and most desirably in the range of $10^{-1}$ to $10^{3\circ}$ C./second. Also, the composition range in which the grains are refined is widened as the cooling rate approaches the upper limit in the aforesaid range. Thus, the grains are further refined.

In the first to eighth copper alloy casting, Pb, Bi, Se, and Te do not only improve the machinability as it is well known, but also improve the conformability and slidability against the counterpart member for friction engaging members such as bearing or the like, thereby improving wear resistance. However, since a large amount of Pb addition will have a negative influence on a human body, it is required to avoid adding Pb more than necessary. Meanwhile, $\gamma$ phase, an extremely hard phase, works as a stress concentration source when machining, like Pb or the like does. When the $\gamma$ phase is dispersed uniformly in the matrix, the machinability can be improved by the synergy effect with Pb or the like. That is, thin shear chips are generated and the chips are segmentalized; and, consequently, a low cutting resistance is realized. Therefore, it is possible to secure industrially satisfactory machinability or the like without adding a large amount of Pb by refining the grains as well as using the γ phase effectively. That is, under the condition that the condition (5) is satisfied, if the contents of Pb or the like are suppressed in the aforesaid ranges and the contents of the elements and the γ phase satisfy the condition (3), industrially satisfactory machinability or the like can be secured with no addition of a large amount of Pb. In addition, if the conditions (13) and (14) are satisfied, that is, if the particles of Pb and Bi as well as the γ phase are small and uniform in size, and are dispersed uniformly in the matrix by grain refinement, the cutting property or the like can be improved more effectively. Generally, Pb, Bi, Se, and Te are added by itself, or in the combination of Pb and Te, Bi and Se, or Bi and Te.

Meanwhile, Pb and Bi are not subject to solid solution at room temperature and are present in the form of Pb and Bi particles. In addition, Pb and Bi are dispersed and exist between the solid phases in a granular shape and a molten state at the melt-solidification stage. Therefore, as the number of Pb and Bi particles increases, cracking is more likely to occur at the melt-solidification stage (due to the tensile stress generated by solidification shrinkage). In addition, since Pb and Bi particles are present mainly at grain boundaries in a molten state even after solidification, if the number of the particles is large, high temperature cracking is highly likely to occur. In solving such problems, it is extremely effective to refine the grains so as to relieve the stress (and make the grain boundary area wider) and to make the Pb and Bi particles smaller and dispersed uniformly. In addition, Pb and Bi have negative effects on the properties of a copper alloy except for machinability, as described above. Since stress is centralized on the Pb and Bi particles, the ductility at room temperature is also impaired (it is needless to say that, when the grains are large, the ductility is impaired synergistically). It is worth noting that the above problem can also be solved by the grain refinement.

In the second, fifth, sixth and eighth copper alloy casting, Sn and Al are added to improve the properties of the casting. Sn improves the mechanical properties (strength or the like), corrosion resistance and wear resistance, and also divides dendrite arms. In addition, Sn widens the composition range of Cu or Zn, in which peritectic reaction occurs, so as to cause peritectic reaction effectively and decreases the stacking fault energy of the alloy. As a result, the grains are granulated and refined more effectively. The above functions of Sn are realized remarkably in the presence of Zr and P. Furthermore, the γ phase generated by Sn suppresses the grain growth after melt-solidification and thus contributes to the grain refinement. The γ phase is an area transformed from a high Sn-concentrated part and such high Sn-concentration part is distributed uniformly and minutely at the melt-solidification stage. Therefore, the γ phase is finely dispersed and suppresses the growth of α phase grains at the high temperature range after solidification. Furthermore, since the γ phase is finely dispersed, the corrosion resistance and wear resistance are also improved. In addition, Al improves strength, flowability, erosion corrosion resistance under high speed of flow, and wear resistance. In the relationship with Sn, Al forms a robust Al—Sn corrosion resistant film on a casting surface so as to improve the corrosion resistance and wear resistance. Like Sn, the above functions are realized effectively by refining the grains with the co-addition of Zr and P. In addition to refine the grains, Sn improves the corrosion resistance, particularly, erosion corrosion resistance, so as to improve the strength and wear resistance. Such effect of Sn can be materialized when the content of Sn reaches 0.05 mass %; effectively when 0.2 mass % is added and more effectively when 0.5 mass % is added. Particularly, when 0.7 or more mass % of Sn is added, an Sn-rich corrosion resistant film is formed under high speed of flow, and thus the significant effect is obtained. On the other hand, since Sn is a low-melting point metal, though depending on the ratio to the other elements such as Cu, Pb, Bi or the like, if more than 4 mass % of Sn is added, it is difficult to obtain a robust casting even in the presence of Zr and P and the casting becomes brittle. The adding amount of Sn is set to be preferably 3.5 mass % or less or 3 mass % or less, and optimally 2.5 mass % or less. Al has the same effect as Sn and improves strength and wear resistance more than Sn does. However, when more than 4 mass % of Al is added, the wear resistance is not so improved any more, but conversely, the casting becomes weak. Therefore, it is desirable that the content of Al be 2.5 mass % or less, or more desirably, 1.5 mass % or less. Meanwhile, when Al is added to improve the corrosion resistance, the adding amount of Al needs to be 0.01 mass %, and preferably 0.03 mass %. When Al is added to improve the erosion corrosion resistance or strength, the adding amount of Al is preferably 0.05 mass % or more, and more preferably 0.1 mass % or more. Therefore, in order that the co-addition of Zr and P works to refine the grains effectively and thus Sn and Al show the functions more effectively, it is required that, considering the relationship with the contents of Zr and P and the relationship with Zn, the conditions (6) to (8) be satisfied in addition that the contents of Sn and Al are in the aforesaid ranges. That is, when Sn and/or Al are added, it is important for grain refinement that f4 (=[Zn]+2.5[Sn]+3[Al]), f5 (=([Zn]+2.5[Sn]+3[Al])/[Zr]) and f6 (=([Zn]+2.5[Sn]+3[Al])/[P]) have given values; therefore, it is required that f4=15 to 42, f5=500 to 20000, and f6=75 to 3000. In order to achieve grain refinement more effectively, it is preferable that f4=20 to 41, f5=800 to 10000, and f6=150 to 1600; more preferable that f4=25 to 40, f5=1200 to 6000, and f6=200 to 1200; and optimal that f4=30 to 39, f5=1600 to 4500, and f6=250 to 1000.

In the third, fifth, seventh and eighth copper alloy casting, As and/or Sb are added mainly to improve the corrosion resistance (particularly, dezincification corrosion resistance). Even though the seawater resistance or corrosion resistance is improved when 0.02 mass % or more of Sb or As is added, in order to make such corrosion resistance-improving effect remarkable, it is preferable to add 0.03 mass % or more of Sb or As. Meanwhile, even when the adding amount of Sb or As exceeds 0.2 mass %, the corresponding effect to the increased adding amount cannot be obtained, and rather, the ductility deteriorates. In addition, the toxicity to human health becomes a problem. In view of such concerns, the adding amount of Sb or As needs to be 0.2 mass % or less, and preferably 0.12 mass % or less.

In the fourth, sixth, seventh and eighth copper alloy casting, Mn, Si and Mg are added mainly to induce the improvement of strength, flowability of molten alloy, the effect of deoxidization and desulfurization, erosion corrosion resistance under high speed of flow, and wear resistance. Meanwhile, scrap materials (wasted heat pipe and the like) are commonly used as part of copper alloy raw materials, and, generally, such scrap materials contain S-component (sulfuric component). If the S-component is contained in the molten alloy, Zr, a grain-refining element, is sulfurized to form a sulfide, and thus the effective grain-refining effect induced by Zr is likely to diminish. In addition, the flowability of molten alloy deteriorates, and thus casting defects such as blowhole, crack or the like can occur easily. In addition to the improvement of corrosion resistance, Mg also improves the flowability of molten alloy during casting even when the scrap material containing S-component is used as a raw material. In addition, Mg can remove the S-component as the less harmful form of MgS. Even if remaining in the alloy, MgS never does harm to the corrosion resistance, and therefore, the deterioration of corrosion resistance caused by the S-component contained in the raw material can be effectively prevented. Furthermore, Mg can effectively prevent the boundary corrosion, which is likely to occur by S-component contained in the raw material due to its tendency of being present at the grain boundary. Moreover, Mn also works to remove the S-component contained in the molten alloy, although the effect is not as much as that of Mg. Also, when the amount of oxygen contained in the molten alloy is large, the grain refining effect of Zr is likely to be lost due to the formation of oxide. However, Mg or the like can prevent Zr from being oxidized as well. When the concentration of S increases in the molten alloy, S is likely to consume Zr. However, if 0.001 mass % or more of Mg is contained in the molten alloy before the charging of Zr, the S-component in the molten alloy is removed or fixed in the form of MgS, therefore the above problem never happens. On the contrary, if Mg is contained excessively, that is, if the content of Mg exceeds 0.2 mass %, it is likely that Mg is oxidized, similar to Zr; the viscosity of molten alloy increases; and the inclusion of oxide or the like generates casting defects. Therefore, when Mg is added, the amount needs to be determined in consideration of these points. If Si is added with Zr, P, Cu and Zn, the stacking fault energy of the alloy decreases, and the effect of grain refinement is realized significantly. In addition, Si improves the flowability of molten alloy, prevents the oxidation of molten alloy, lowers the melting point, and improves the corrosion resistance, in particular, dezincification corrosion resistance and stress corrosion cracking resistance. Furthermore, Si contributes to the improvement of machinability and the mechanical properties such as tensile strength, proof stress, impact strength, fatigue stress or the like. The above effects induce a synergy effect for the grain refinement of a casting. Still furthermore, if Mn and Si are added together, an intermetallic compound of Mn—Si is formed, thereby improving the wear resistance. Considering these points, the content of Mn, Si and Mg is determined in the aforesaid ranges.

In order for the first to eighth copper alloy casting to secure sufficient corrosion resistance, wear resistance, strength or the like, it is required that each copper alloy casting have the aforesaid alloy composition and satisfy the condition (4). That is, the first to eighth copper alloy casting need to form a phase structure (metal structure), in which the total content of α phase and γ phase occupy 85% or more (preferably 90% or more, more preferably 95% or more, and optimally 98% or more). However, if the content of γ phase is excessive, the corrosion resistance is impaired due to the occurrence of selective corrosion in phases. In addition, even though the γ phase improves wear resistance and erosion corrosion resistance, the presence of the γ phase can also be a cause of impairing ductility. Therefore, in order to secure the strength, wear resistance and ductility in a balanced manner while keeping the corrosion resistance, the content of γ phase needs to be 25% or less by the area ratio, and preferably 15% or less (more preferably 0.1 to 10%). When the grains are refined by the co-addition of Zr and P, the γ phase is divided and spherically shaped inevitably, and further, the γ phase can be distributed uniformly in the matrix, thereby improving the machinability, mechanical properties and wear resistance (slidability) considerably. In order to obtain such property-improving effects, the attention should be focused on the fact that 1% of the ratio (area ratio) occupied by γ phase when the particles of Pb and Bi and the γ phase are dispersed uniformly in the matrix corresponds to 0.05 mass % of the adding amount of Pb. That is, it is further required to satisfy the condition (3), that is, the content (area ratio) of γ phase and the content of Pb or the like have the following relationship: f3=0.05[γ]+([Pb]+[Bi]+[Se]+[Te])=0.45 to 4, preferably f3=0.6 to 2, and more preferably f3=0.95 to 1.5. In order to further improve the machinability or the like, it is preferable to satisfy the conditions (13) and (14), that is, the γ-phase and the particles of Pb and Bi be dispersed uniformly in the matrix.

In the second, fifth, sixth and eighth copper alloy casting, in order to obtain the above-described phase structure and to satisfy the condition (5), it is preferable that the contents of Sn and Al are adjusted in consideration of the relation with Cu and the other additional elements. That is, in order to realize the grain refinement more effectively, it is preferable that the content of Sn or the like is determined to satisfy the conditions (1) and (6), in addition to (2), (3), (4), (7) and (8). Alternatively, it is preferable that the maximum value of f1 (=[Cu]−3[P]+0.5([Pb]+[Bi]+[Se]+[Te])−0.5[Sn]−1.8[Al]−([As]+[Sb])+[Mn]−3.5[Si]−0.5[Mg]) or the minimum value of f4 (=[Zn]+2.5[Sn]+3[Al]) be set as already described in order to secure more excellent corrosion resistance (erosion corrosion resistance) and wear resistance, considering the relation with the contents of Cu, a main component, or the like. Meanwhile, in consideration of the elongation, corrosion resistance and castability attributed to the γ phase, it is preferable that the minimum value of f1 or the maximum value of f4 be also limited and set as described previously. When securing the above properties, the concentration of Sn varies with the concentration of Cu.

In the first to eighth copper alloy casting, a high-quality casting is achieved when the condition (5) is satisfied, that is, the mean grain size in the macrostructure during melt-solidification is made to be 250 μm or less (preferably 100 μm or less, 60 μm or less in the microstructure), as well as the grains are refined by the addition of Zr and P. In addition, a casting manufactured by continuous casting methods such as horizontal continuous casting, upward (upcast) or the like can be provided at a practical level. If the grains are not refined, at least one or more times of heat treatment is required to eliminate the dendrite structure that is unique to a casting; to prevent Sn from segregating; to divide the γ-phase into spherical shape; or the like. In addition, the surface condition is bad when the grains are coarsened. However, if the grains are refined as described above, the aforesaid heat treatment becomes unnecessary since the segregation of Sn is minimized to a microstructural level. Thus, the surface condition also becomes good. Furthermore, the γ phase exists in the grain boundary when precipitated. The length of the phase gets shorter as the grains are dispersed finer and more uniformly; therefore, a particular processing to divide the γ phase is not required, or can be kept to the minimum even if it becomes necessary. As described, the number of the required processes can be limited considerably and thus, manufacturing cost can be reduced as much as possible. Meanwhile, if the condition (5) is satisfied, excellent copper alloy properties can be obtained without accompanying the following problems; That is, if the size of γ phase containing a large amount of Sn, a low-melting point metal, is irregular and lacks uniformity, or the γ phase is not distributed uniformly, the difference in strength between the α-phase in the matrix and the γ-phase causes cracks and impairs the ductility. Furthermore, the particles of Pb or Bi exist by nature at the border between the α phase and other phases such as γ phase or the like, or at the grain boundary. When the phase is large, therefore, cracks during solidification are highly likely to be generated.

Meanwhile, Zr and P are added together only to refine the grains, and thus Zr and P do not impair the inherent properties of the copper alloy. In addition, since the grains are refined by the co-addition of Zr and P, the copper alloy can secure the same or better properties as a copper alloy having the same composition except for Zr and P. In order to make the mean grain size as fine as described above during melt-solidification, the contents of Zr and the like need to be determined to satisfy the conditions (1) to (4) for the first, third, fourth and seventh copper alloy casting and the conditions (1) to (4) and (6) to (8) for the second, fifth, sixth and eighth copper alloy casting.

In the first to eighth copper alloy casting, scrap materials can be used as raw materials. When such scrap materials are used as raw materials, it is inevitable that impurities are contained, which is allowed in a practical casting process. However, if the scrap material is nickel plating material or the like, and Fe and/or Ni are contained as the inevitable impurities, it is required to restrict the contents of Fe and/or Ni. That is, if the contents of Fe and/or Ni are large, Zr and P, which are effective for the grain refinement, are consumed by Fe and/or Ni, thereby deterring the grain refinement. Therefore, when either Fe or Ni is contained, it is preferable to restrict the contents of Fe and Ni within a range, in which the grain refinement is not deterred. Specifically, when either Fe or Ni is contained, it is preferable that the content of Fe or Ni be restricted to be 0.2 mass % or less (more preferably 0.1 mass % or less and optimally 0.05 mass % or less). When both Fe and Ni are contained, it is preferable that the total content of Fe and Ni be restricted to be 0.25 mass % or less (more preferably 0.13 mass % or less, and optimally 0.08 mass % or less).

Since the first to eighth copper alloy castings have extremely excellent machinability, strength, wear resistance (including slidability) and corrosion resistance due to the grain refinement and the uniform dispersion of Pb particles or the like, the first to eighth copper alloy castings can be used practically, preferably as water contact metal fittings (for example, water faucet of a water supply pipe, metal fitting for water supply and discharge, valves, joints, stem, parts for boiler, or the like) used continuously or temporarily in contact with water, friction engaging member (for example, bearing, gear, cylinder, bearing or the like) which makes a relative movement to a facing member (rotating shaft or the like) continuously or temporarily in contact with the facing member or the like, or the structural material thereof.

In addition, the invention proposes a method of casting a copper alloy casting having excellent machinability, strength, wear resistance and corrosion resistance, in which Zr (contained to refine the grains further and stably) is added in the form of a copper alloy containing Zr right before pouring or at the final stage of raw material melting, and thus Zr is not added in the form of oxide and/or sulfide during casting. Cu—Zr alloy, Cu—Zn—Zr alloy or an alloy containing one or more elements selected from P, Mg, Al, Sn, Mn and B in addition to the Cu—Zr or Cu—Zn—Zr alloys (base material alloys) is preferable for the copper alloy containing Zr.

That is, in the casting process of the first to eighth copper alloy castings, the losing amount of Zr when added can be as minimized as possible by adding Zr right before pouring in the form of an intermediate copper alloy of granular, thin plate, rod, or wire. This way, Zr is prevented from being added in the form of oxide and/or sulfide during casting, otherwise it is impossible to secure the amount of Zr required and sufficient for the grain refinement. In addition, when Zr is added right before pouring as described above, since the melting point of Zr is 800 to 1000° C. higher than that of the copper alloy, it is preferable to use a granular intermediate alloy (grain diameter: about 2 to 50 mm), a thin plate intermediate alloy (thickness: about 1 to 10 mm), a rod-like intermediate alloy (diameter: about 2 to 50 mm) or a wire-like intermediate alloy, and each of them is a low melting point alloy having the melting point close to the melting point of the copper alloy and containing a lot of necessary components (for example, Cu—Zn alloy or Cu—Zn—Zr alloy containing 0.5 to 65 mass % of Zr, or an alloy containing one or more element selected from P, Mg, Al, Sn, Mn and B (the content of each element: 0.1 to 5 mass %) added to a base material alloy Cu—Zn or Cu—Zn—Zr. Particularly, in order to decrease the melting point so as to facilitate melting and prevent the loss of Zr, it is preferable to use the intermediate alloy in the form of a Cu—Zn—Zr alloy containing 0.5 to 35 mass % of Zr and 15 to 50 mass % of Zn (preferably a Cu—Zn—Zr alloy containing 1 to 15 mass % of Zr and 25 to 45 mass % of Zn). Although depending on the mixing ratio of Zr to P, Zr impairs electrical conductivity and thermal conductivity, which are the inherent properties of a copper alloy. However, if the amount of Zr, not in the form of oxide nor sulfide, is 0.045 mass % or less (particularly 0.019 mass % or less), such reduction of electrical conductivity and/or thermal conductivity rarely happens and, even if happens, the reduction is very small compared with the alloy containing no Zr.

Furthermore, in order to obtain the first to eighth copper alloy castings satisfying the condition (5), it is desirable to define the casting conditions properly, in particular, pouring temperature and cooling rate. That is, with respect to the pouring temperature, it is preferable to determine the temperature to be 20 to 250° C. (more preferably 25 to 150° C.) higher than the liquidus temperature of the copper alloy. That is, it is preferable that (liquidus temperature+20° C.)≤pouring temperature≤(liquidus temperature+250° C.), and it is more preferable that (liquidus temperature+25° C.)≤pouring temperature≤(liquidus temperature+150° C.). Generally, the pouring temperature is 1150° C. or less, preferably 1100° C. or less, and more preferably 1050° C. or less. Even though there is no limitation on the minimum pouring temperature as long as the molten alloy can reach every corner of a mold, the grains tend to be more refined as the pouring temperature is lowered. Meanwhile, it should be understood that these temperature conditions vary with the mixing amount of the alloying elements.

Since the grains are refined during melt-solidification, the copper alloy castings according to the invention are resistant to the shrinkage during solidification, and the generation of defects such as crack or the like can be prevented as much as possible. In addition, in terms of holes or porosity generated during solidification, robust castings including no casting defect or the like can be obtained since gas can be easily escaped. That is, the surface is smooth and shrinkage cavity becomes as shallow as possible since no defect such as porosity or the like is included and dendrite network is not formed.

The dendrite structure of the copper alloy castings according to the invention, which is crystallized during solidification, is not a typical dendrite casting structure, but has divided arms preferably in the form of circular, oval, polygonal or cross-like shape. As a result, the flowability of molten alloy improves, and the molten alloy can reach every corner of a mold even when the mold is thin-walled and complexly shaped.

The copper alloy casting of the invention can secure industrially satisfactory machinability or the like without a large amount of addition of a machinability-improving element such as Pb, which acts as a chip breaker, by the grain refinement and by the uniform dispersion of phases other than α phase (γ phase generated by Sn), the segregated Sn or the like, and Pb particles or the like. Also the copper alloy casting of the invention can have considerably improved strength, wear resistance (slidability) and corrosion resistance enhanced by the other components. Therefore, the copper alloy casting of the invention can be preferably used as water contact metal fittings (for example, water faucet of a water supply pipe, valves, cocks, joints, flanges, in-house built device, equipments for sewerage, joint clip, parts for boiler, or the like) used continuously or temporarily in contact with water (water from a water faucet or the like), friction engaging member (for example, bearing, gear, cylinder, bearing retainer, impeller, parts for pumps, bearing or the like) making a relative movement to a facing member (rotating shaft or the like) continuously or temporarily in contact with the facing member or the like, or the structural material thereof.

Still furthermore, according to a method of the invention, since the disadvantages caused by the addition of Zr in a form of oxide and/or sulfide do not occur, the grains are refined by the co-addition of Zr and P, thus the copper alloy casting can be cast efficiently and satisfactorily.

BRIEF DESCRIPTION OF THE DRAWINGS

FIG. 1 includes photos of etched surfaces (cross-sectional surfaces) of an embodiment No. 16, in which FIG. 1A shows a macrostructure, and FIG. 1B shows a microstructure.

FIG. 2 includes photos of etched surfaces (cross-sectional surfaces) of a comparative example No. 204, in which FIG. 2A shows a macrostructure, and FIG. 2B shows a microstructure.

FIG. 3 includes X-ray micro-analyzer photos of the etched surface (cross-sectional surface) of the embodiment No. 16, in which FIG. 3A shows a composition image; FIG. 3B shows the distribution of Sn; and FIG. 3C shows the distribution of Pb.

FIG. 4 includes X-ray micro-analyzer photos of the etched surface (cross-sectional surface) of the comparative example No. 204, in which FIG. 4A shows a composition image; FIG. 4B shows the distribution of Sn; and FIG. 4C shows the distribution of Pb.

FIG. 5 includes cross sectional views showing a result of the tatur shrinkage test, in which FIG. 5A shows 'good' test result; FIG. 5B shows 'fair' test result; and FIG. 5C shows 'poor' test result.

FIG. 7 includes front views showing test pieces cast in the casting crack test, in which FIG. 7A shows a test piece with no crack; FIG. 7B shows a test piece with a minute crack; and FIG. 7C shows a test piece with a noticeable crack.

FIG. 8 includes perspective views showing the forms of chips generated during the machining test.

BEST MODE FOR CARRYING OUT THE INVENTION

Embodiment

Figure 3:
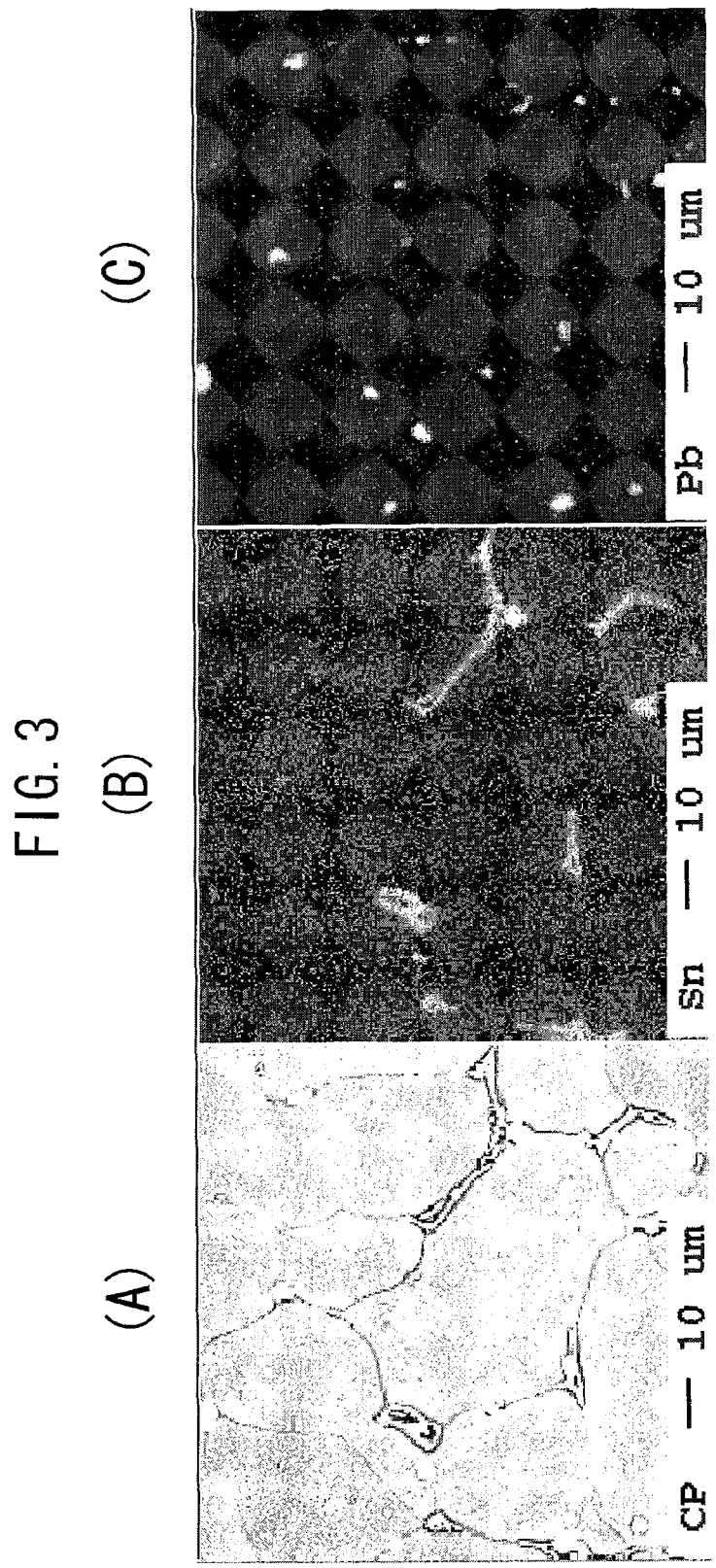

As embodiments, the alloying materials listed in Tables 1 to 4 are melted in an electric furnace, and then each molten alloy obtained is poured into a iron-made mold preheated up to 200° C. so as to cast cylindrical (diameter: 40 mm, and length: 280 mm) castings (hereinafter referred to as 'embodiments') Nos. 1 to 107. In this case, Zr is added to each molten alloy in a granular form of Cu—Zn—Zr alloy (a cubic body having several mm long sides) right before pouring in order to prevent Zr from being added in the form of oxide and/or sulfide. In addition, the pouring temperature is set at 100° C. above the liquidus line temperature of each copper alloy.

In addition, as comparative examples, the alloying materials listed in Table 5 are melted in an electric furnace, and then each molten alloy is poured into an iron-made mold preheated up to 200° C. under the same conditions as those of the embodiments so as to cast cylindrical (diameter: 40 mm, length: 280 mm) castings (hereinafter referred to as 'comparative examples') Nos. 201 to 222.

A No. 10 specimen pursuant to JIS Z 2201 is taken from each embodiment and each comparative example, and then tensile strength test is performed on each specimen by an AMSLER universal testing machine in order to measure the tensile strength (N/mm$^2$), 0.2% proof stress (N/mm$^2$), elongation (%), and fatigue strength (N/mm$^2$). The results are illustrated in Tables 6 to 10.

In order to verify the wear resistance (slidability) of the embodiments and the comparative examples, wear test is performed as follows.

First of all, a ring specimen having the outer diameter of 32 mm and the thickness (axial direction length) of 10 mm is obtained from each embodiment and each comparative example by machining, drilling or the like. Next, the ring specimen is fit with a rotating shaft and then rotated with a load of 25 kg applied to the ring specimen by making a SUS304-made roll (outer diameter 48 mm) in contact with the outer circumferential surface of the ring specimen. After that, the rotating shaft is rotated at a speed of 209 r.p.m. while multipurpose oil is being dropped onto the outer circumferential surface of the specimen. When the specimen rotates hundred thousand times, the rotation of the specimen is stopped, and the mass difference before and after the rotation, that is, wear loss (mg) is measured. It can be said that a copper alloy showing smaller wear loss has more excellent wear resistance. The results are shown in Tables 6 to 10.

In order to verify the corrosion resistance of the embodiments and the comparative examples, the following erosion corrosion tests I to IV and the dezincification corrosion test designated as 'ISO 6509' are performed.

For the erosion corrosion tests I to IV, test liquid (30° C.) is sprayed at a specimen taken from each casting through a 1.9 mm diameter nozzle at a speed of 11 m/sec in a perpendicular direction to the axes of the specimen. After a given time, the mass loss (mg/cm$^2$) is measured. As the test liquid, 3% saline solution is used for test I, a mixed saline solution of 3% saline solution and CuCl$_2$.2H$_2$O (0.13 g/L) for test II, a mixed liquid of Sodium Hypochlorite Ingestion (NaClO) with a small addition of hydrochloric acid (HCl)

for test III, and a 3% saline solution containing glass beads of 0.115 mm in average diameter (5 vol %) for test IV. The mass loss is the mass difference per one square centimeter (mg/cm$^2$) between the mass of the original specimen (before the test) and that of the specimen after "T" hours of being sprayed at with the test liquid. The testing time "T" (duration of spraying) is 96 hours for test I to III, and 24 hours for test IV. The results of the erosion corrosion test are illustrated in Tables 6 to 10.

For the dezincification corrosion test of 'ISO 6509', a specimen taken from each embodiment and each comparative example is embedded in a phenolic resin material so that the exposed surface of the specimen is perpendicular to the expanding direction of the specimen; and then the surface is polished with Emery paper up to No. 1200. After that, the surface is ultrasonic-cleaned in pure water and then dried. The corrosion test specimen thus prepared is soaked in an aqueous solution of 1.0% Cupric Chloride Dihydrate (CuCl$_2$.2H$_2$O) for 24 hours at 75° C., and then the specimen is taken out of the aqueous solution. After that, the maximum depth of dezincification corrosion, that is, the maximum dezincification corrosion depth (μm) is measured. The results are illustrated in Tables 6 to 10.

In addition, in order to verify the machinability of the embodiments and the comparative examples, the following cutting test is performed, and the main cutting force (N) is measured.

That is, each casting of the invention is cut on the outer circumferential surface under the dry condition by a lathe having a point nose straight tool (rake angle: −6°, and nose radius: 0.4 mm) at a cutting speed of 100 m/minute, a cutting depth of 1.5 mm, and a feed rate of 0.11 mm/rev. The cutting force is measured by three component dynamometers attached to the bite and then calculated into the main cutting force. The results are shown in Tables 6 to 10.

Furthermore, the state of chips generated in the cutting test is observed, and the machinability of the copper alloy castings is determined by classifying the chips into seven categories on the basis of the shapes of chips: (a) trapezoidal or triangular small segment shape (FIG. 8A), (b) tape shape having a length of 25 mm or less (FIG. 8B), (c) acicular shape (FIG. 8C), (d) tape shape as long as 75 mm or less (excluding (b)) (FIG. 8D), (e) spiral shape having three or less windings (FIG. 8E), (f) tape shape longer than 75 mm (FIG. 8F), and (g) spiral shape having more than three windings (FIG. 8G). The results are shown in Tables 6 to 10. That is, when the chips have the shapes of (f) and (g), the chips are hard to handle (recovery, recycling or the like), and also cause the following troubles: the chips get tangled with the bite of a cutting tool; cut surfaces are damaged; or the like. As a result, satisfactory cutting work cannot be performed. In addition, when the chips have the shapes of (d) and (e), though they do not cause such serious troubles as those of (f) and (g), the chips of (d) and (e) are still hard to handle. They are likely to get tangled with the bite or cut surfaces may be damaged when a continuous cutting work is performed. On the other hand, when the chips have the shapes of (a) to (c), the troubles as described above are not induced, and the chips can be easily handled since they are not bulky unlike the chips of (f) and (g). However, in case the chips have the shape of (c), the chips are likely to creep in on the sliding table of a machine tool such as a lathe or the like under a certain working condition and cause mechanical problems, or the chips can be hazardous as they stick the operator in the eye or the finger. Therefore, in the determination of machinability, the shapes of (a) and (b) (particularly (a)) are graded as the best; the shape of (c) is graded as the second best; the shapes of (d) and (e) are graded as industrially acceptable; and the shapes of (f) and (g) are graded as unacceptable. In Tables 6 to 10, chips of (a) and (b) graded as the best are denoted as "◉"; chips of (c) graded as the second best are denoted as "◯"; chips having the acceptable shapes of (d) and (e) are denoted as "Δ"; and chips of (f) and (g) graded as unacceptable are denoted as "x". Among the embodiments, on which the cutting test is performed, no chips denoted as "x" are observed.

From the test results described above, it is verified that the embodiments are superior in machinability, mechanical properties (strength, elongation or the like) wear resistance and corrosion resistance to the comparative examples. In addition, although it is commonly considered that elongation is lowered by grain refinement, the result of the tensile strength test shows that the elongation of the copper alloy casting of the invention does not decrease by the grain refinement, but rather improves.

In addition, in order to evaluate cold workability of the embodiments and the comparative examples, the following cold compression test is performed.

That is, a cylindrical specimen of 5 mm in diameter and 7.5 mm in length is machined by a lathe from each embodiment and each comparative example, and then compressed by the AMSLER universal test machine. After that, the cold workability is evaluated on the basis of the relation between the existence of cracks and the compression rate (processing rate). The results are illustrated in Tables 6 to 8 and 10. In the tables, specimens having cracks at the compression rate of 35% are denoted as 'x' to indicate poor cold workability; specimens having no crack at the compression rate of 50% are denoted as 'O' to indicate good cold workability; and specimens having no crack at the compression rate of 35%, but having cracks at the compression rate of 50% are denoted as 'Δ' to indicate fair cold workability. The cold compression workability can also be appreciated as caulking workability, and castings denoted as 'O' can be caulked easily and precisely; castings denoted as 'Δ' can be caulked fairly well; and castings denoted as 'x' cannot be caulked properly. It is verified that all the embodiments, on which the cold compression workability test is performed, are evaluated 'Δ' or 'O', that is, they have excellent cold workability or caulking workability.

Furthermore, the metal structure (phase structure) after melt-solidification of each embodiment and each comparative example at room temperature is verified, and the area ratios (%) of α phase and γ phase are measured by image analysis. That is, the structure of each casting, magnified 200 times by an optical microscope, is expressed in the binary system with an image processing software 'WinROOF', and then the area ratio of each phase is measured. The area ratio is measured in three different fields, and the average value of the three area ratios is regarded as the phase ratio of each phase. The results of the metal structures are illustrated in Table 1 to 5, and the results of the total area ratio of α and γ phases and the area ratio of γ phase are illustrated in Tables 6 to 10. All the embodiments satisfy the condition (4). In addition, Tables 1 to 5 show what the primary crystal was during melt-solidification in casting process. All the embodiments satisfy the condition (9). Meanwhile, the embodiments containing a large amount of β phase are annealed in order to increase the amount of α phase, and thus the embodiments can have excellent properties due to the increased ratio of α phase.

Still furthermore, the mean grain size (μm) of each embodiment and each comparative example during melt-solidification is measured. That is, a casting is cut, and the cross-sectional surface is etched by nitric acid. After that, the mean grain size of the microstructure displayed on the etched surface is measured. The measurement is based on the comparative method for estimating average grain size of wrought copper and copper alloys according to JIS H0501, in which grains having the diameter of more than 0.5 mm are observed by naked eyes, and grains having the diameter of 0.5 mm or less are magnified 7.5 times and then observed after the cut surface is etched by nitric acid. In addition, grains having the diameter of less than approx. 0.1 mm are etched by a mixed liquid of hydrogen peroxide and ammonia water and then magnified 75 times by an optical microscope for observation. The results are illustrated in Tables 6 to 10, and all the embodiments satisfy the condition (5). Meanwhile, in the comparative example No. 222 containing a proper amount of Zr but no content of P, the grains are refined only slightly. From this standpoint, it can be understood that the single addition of Zr is not sufficient enough to work on the grain refinement, and it is required to add Zr and P together to achieve grain refinement significantly. Furthermore, it is verified that the embodiments also satisfy the conditions (10) to (14). FIG. 1 to FIG. 4 are displayed as an example.

FIG. 1 includes a photo of the macrostructure (FIG. 1A) and a photo of the microstructure (FIG. 1B) of the embodiment No. 16, and FIG. 2 includes a photo of the macrostructure (FIG. 2A) and a photo of the microstructure (FIG. 2B) of the comparative example No. 204. It is evident from FIG. 1 and FIG. 2 that the comparative example No. 204 does not satisfy the conditions (11) and (12), but the embodiment No. 16 satisfies the conditions (11) and (12).

Figure 4:
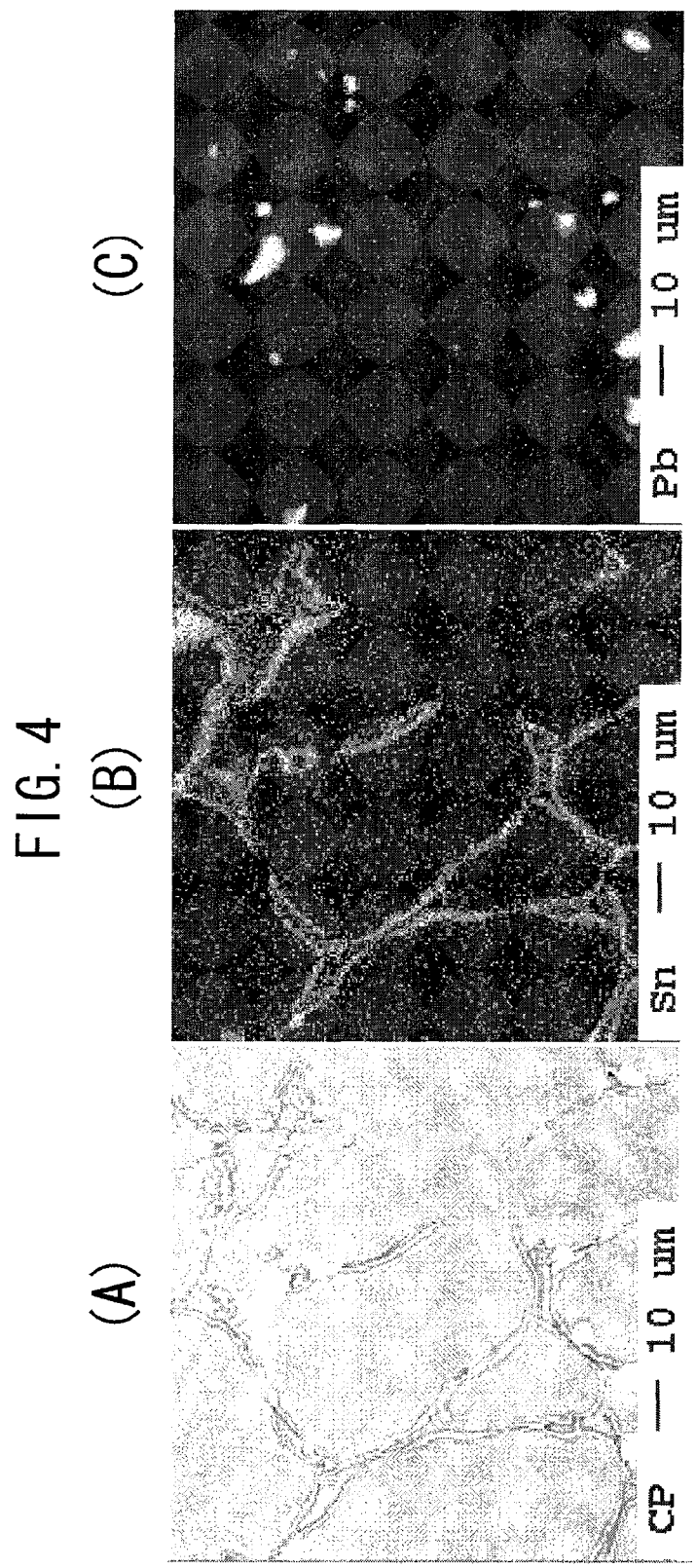

FIG. 3 includes X-ray micro-analyzer photos of the embodiment No. 16, in which FIG. 3A shows a composition image; FIG. 3B shows the distribution of Sn; and FIG. 3C shows the distribution of Pb particles. FIG. 4 includes X-ray micro-analyzer photos of the comparative example No. 204, in which FIG. 4A shows a composition image; FIG. 4B shows the distribution of Sn; and FIG. 4C shows the distribution of Pb particles. It is evident from FIG. 3 that, in the embodiment No. 16, the high Sn-concentrated areas (white areas in FIG. 3B) and the Pb particles (white areas in FIG. 3C) are small and uniform in size, and are distributed evenly, thereby satisfying the conditions (13) and (14). On the other hand, in the comparative example No. 204, as shown in FIG. 4, the high Sn-concentrated areas (white areas in FIG. 4B) and the Pb particles (white areas in FIG. 4C) are not uniform in size and are distributed unevenly, thereby not satisfying the conditions (13) and (14).

In addition, the comparative example No. 204 has almost the same composition as that of the embodiment No. 16 except that the content of Zr does not reach the lower limit of the above-described proper range. From this point of view, it can be understood that the grains can be refined effectively and the particles of Pb or the like can be made smaller and be dispersed when a proper amount of Zr and P is co-added under the above-described conditions. Furthermore, according to the results of the wear test (wear loss) and the cutting test, it is evident that the embodiment No. 16 is superior to No. 204 in wear resistance and machinability. Therefore, it can be understood that satisfying the conditions (11) to (14) is an important factor to further improve the wear resistance (slidability) and machinability.

From the above facts, it is verified that, when the embodiment contains each alloying component in the above-described range and satisfies the conditions (1) to (5) (additionally the conditions (6) to (8) in the case of the second, fifth, sixth and eighth copper alloy casting), the embodiment has much more improved machinability, strength, elongation, wear resistance and corrosion resistance than the comparative example not satisfying at least any of the above conditions. In addition, it is also verified that the improved properties as described above can be achieved more effectively if the conditions (9) to (14) are satisfied in addition to the aforesaid conditions.

Still furthermore, it is considered that the castability can also be improved by satisfying the condition (5), that is, by refining the grains. In order to verify this, the following Tatur shrinkage test and casting-cracking test are performed.

Figure 5:
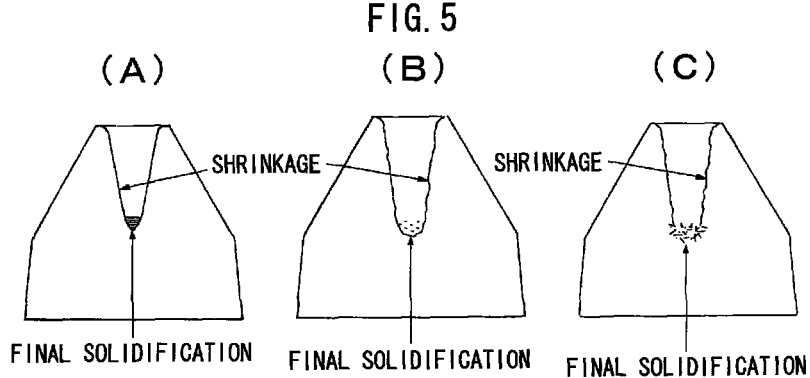

That is, Tatur shrinkage test is conducted by using the molten alloys (of the copper alloy materials having the compositions listed in Tables 1 to 5 and poured at the same temperature) which are used in casting the embodiments and the comparative examples. Then the castability is evaluated by examining the shapes of internal shrinkage area and the existence of casting defects such as porosity, hole, shrinkage cavity or the like in the vicinity of the internal shrinkage area. The castability is evaluated as 'good' for a casting having a smooth internal shrinkage area and no defect such as porosity or the like in the final solidification area as shown in FIG. 5A; 'poor' for a casting having a remarkably uneven internal shrinkage area and defects such as porosity or the like in the final solidification area as shown in FIG. 5C, and 'slightly poor' for a casting evaluated neither 'good' nor 'poor' as shown in FIG. 5B. The results are illustrated in Tables 6 to 10. In the tables, 'good' is denoted as '○'; 'slightly poor' is denoted as 'Δ'; and 'poor' is denoted as 'x'. In addition, the grain size in the macrostructure is measured for each casting obtained by the Tatur shrinkage test. The results are illustrated in Tables 6 to 10. In the tables, castings having the grain size of 100 μm or less are denoted as '○'; castings having the grain size in the range of 100 to 250 μm are denoted as 'Δ'; and castings having the grain size of more than 250 μm are denoted as 'x'. The results correspond to the results of the mean grain size measured for the embodiments and the comparative examples as described above.

From Tables 6 to 10 showing the results of the Tatur Shrinkage Test, it is verified that, although a few embodiments are graded as 'slightly poor', most of the embodiments have much more excellent castability due to the grain refinement than the comparative examples, most of which are graded 'poor'.

Figure 6:
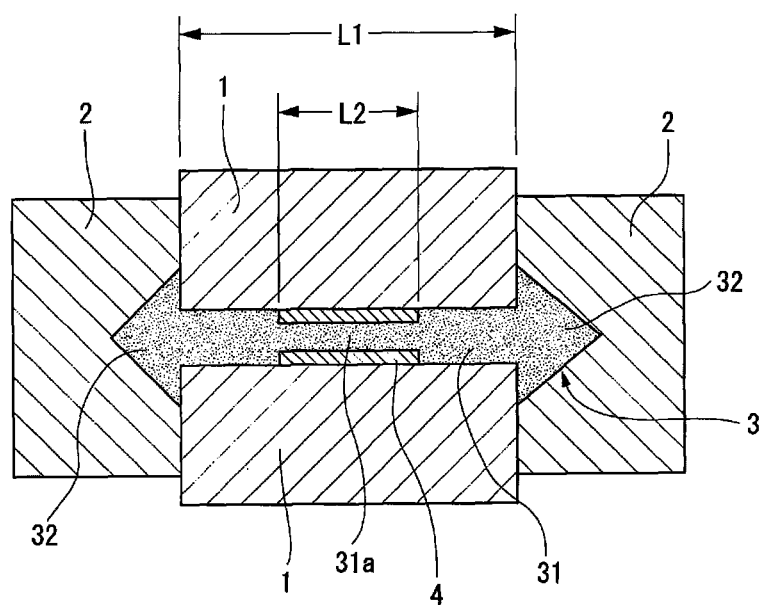
FIG. 6 is a front view of a vertically cross-sectioned test piece showing the casting state in a casting crack test.

Still furthermore, in the casting crack test, a test piece 3 is cast by using the top mold 1 and the bottom mold 1, and the right mold 2 and the left mold 2 as shown in FIG. 6. Then the castability is examined whether cracks occur in the test piece 3. That is, the test piece 3 is cast in a shape of a two-headed arrow consisting of a band plate 31 in the midsection with two triangular plates 32 and 32 affixed to the both ends of the band plate. The central part of the band plate 31 is considered as crack judgment area 31a (Castability is measured by the cracks occurred in the area). The band plate 31 is cast in the cavity between the top and bottom molds (1 and 1). Inside the molds are partly placed heat insulation material 4 so that the crack judgment area 31a is cast in this particular area of the cavity surrounded by the heat insulation material 4 (where solidification slows down). There are two other cavities formed by the right and left molds (2 and 2) where the triangular plate 32 is cast in each mold. When a molten alloy is poured into the cavities, the solidification in the crack judgment area 31a proceeds slower than the other areas due to the heat insulation material 4. When the band plate 32 shrinks in the longitudinal direction by solidification, the triangular plates 32 and 32 restrict the shrinkage. Therefore, the stress arising from the shrinkage is centralized in the crack judgment area 31*a* where the molten alloy is solidified slower. As such, castability is evaluated by the presence of cracks in the crack judgment area 31*a*. In the casting crack test, L1, the length of the band plate 31, and L2, the length of the crack judgment area 31*a* are set to be 200 mm and 100 mm, respectively. As conducted in the Tatur Shrinkage Test, the test piece 3 is cast with a molten alloy having the same composition and the same temperature as the molten alloy used for the embodiments (Nos. 1 and 2) and the comparative examples (Nos. 204 to 209, 211, 213, 215, and 219 to 221). The results are illustrated in Tables 6 to 8 and 10. Upon the determination of castability, when a noticeable crack 33*a* in the crack judgment area 31*a*, as shown in FIG. 6C, is visually examined in a test piece casting, the casting is evaluated to have poor castability, thereby being denoted as 'x'. In addition, when no crack is observed in the crack judgment area 31*a* with naked eye or even with five-time magnification glass, as shown in FIG. 6A, the casting is evaluated to have excellent castability, thereby being denoted as '○'. Furthermore, as shown in FIG. 6B, when a test piece casting, in which no noticeable crack 33*a* can be found in the crack judgment area 31*a* by a visual examination, has a minor crack 33*b* observed with five-time magnification glass is evaluated to have normal castability, thereby being denoted as 'Δ'. All the embodiments, on which the casting crack test is performed, are graded as '○', and thus verified to have excellent castability.

Meanwhile, if the solid phase is granulated in a semi-solid metal state, naturally, the semi-solid metal castability becomes excellent, and thus semi-solid metal casting can be performed satisfactorily. The flowability of a molten liquid containing solid phases at the final stage of solidification depends mainly on the shape of the solid phase and the viscosity or composition of the liquid phase in a semi-solid metal state. Specifically, the casting moldability (a property determining whether or not a robust casting can be obtained even when a precision casting or a casting of a complicated shape is required) is more influenced by the former, that is, the shape of the solid phase. If the solid phase begins to form a network of dendrite in a semi-solid metal state, the casting moldability deteriorates since the molten liquid containing the solid phase is hard to fill in every corner of a mold. Therefore, a precision casting or a casting of a complicated shape is difficult to be realized. Meanwhile, when the solid phase is granulated in a semi-solid metal state, and when the shape of the solid phase becomes more spherical (more circular in two-dimension) and smaller, castability including the semi-solid metal castability becomes more excellent. As a result, a robust precision casting or a casting of complicated shape can be obtained (Naturally, high-quality semi-solid metal castings can be obtained). Therefore, the semi-solid metal castability can be evaluated by examining the shape of the solid phase in a semi-solid metal state. Also, the other castability including complicated-shape castability, precision castability and semi-solid metal forgeability can be evaluated by the semi-solid metal castability. In general, the semi-solid metal castability can be graded as good when, in a semi-solid metal state including 30 to 80% of solid phase, the dendrite network is divided in the crystal structure and the two-dimensional shape of the solid phase is circular, substantially circular, oval, cross-like or polygonal; and further, in a semi-solid metal state including 60% of solid phase particularly, the semi-solid metal castability can be graded as excellent either when the mean grain size of the solid phase is 150 μm or less (preferably 100 μm or less, and more preferably 50 μm or less), or when the average maximum length of the solid phase is 300 μm or less (preferably 150 μm or less, and more preferably 100 μm or less.

In addition, in order to evaluate the semi-solid metal castability of the embodiments in comparison to the comparative examples, the following semi-solid metal castability test is performed.

In the semi-solid metal castability test, the raw materials used for casting the embodiments and the comparative examples are charged into a crucible; heated up to the temperature where the raw materials come into the semi-solid metal state (solid phase ratio: about 60%). The semi-solid metal molten thus obtained is then held at the aforesaid temperature for 5 minutes and quenched rapidly (by water cooling) afterwards. Then, the shape of the solid phase in the semi-solid metal state is examined so as to evaluate the semi-solid metal castability. The results are illustrated in Tables 6 to 8 and 10. It is verified that each embodiment shows excellent semi-solid metal castability. Meanwhile, in the tables, a casting having the mean grain size of 150 μm or less of the solid phase or the mean maximum grain length of 300 μm or less is denoted as '○' to indicate excellent semi-solid metal castability; a casting having a grain size bigger than the aforesaid, but having no dendrite network therein is denoted as 'Δ' to indicate industrially satisfactory semi-solid metal castability; and a casting having dendrite network therein is denoted as 'x' to indicate poor semi-solid metal castability.

In addition, a new casting (hereinafter referred to as 'recycled casting') is cast by using the copper alloy casting No. 25 (hereinafter referred to as 'casting product'), which was obtained as an embodiment, as a raw material. That is, the casting product (the copper alloy casting No. 25) is re-melted at the temperature of 1000° C. under a charcoal coating and held for 5 minutes. Then Cu—Zn—Zr alloy containing 3 mass % of Zr is added to the molten alloy to compensate for the Zr loss caused by oxidation while melting, based on the assumption that the Zr loss would be 0.002 mass %. After that, the molten alloy made from the casting product is poured into a mold. The recycled casting thus obtained contains almost the same amount of Zr (0.009 mass %) as that of the casting product No. 25 used as the raw material. The mean grain size of the recycled casting (30 μm) is also almost the same as that of the casting product No. 25. From these points, for the copper alloy casting of the invention, it is verified that the surplus or unnecessary parts such as runner or the like, which are generated during the casting process, can be effectively reused as a recycling raw material without impairing the effect of grain refinement. Therefore, such surplus or unnecessary parts including runner or the like can be charged during a continuous operation as a replenishing material, which makes the continuous operation extremely efficient and effective costwise as well.

TABLE 1

| Casting No. | | Alloy Composition (mass %) | | | | | | | | f1 | f2 | f3 | f4 | f5 | f6 | Primary Crystal | Metal Structure |
|---|---|---|---|---|---|---|---|---|---|---|---|---|---|---|---|---|---|
| | | Cu | Zn | Zr | P | Sn | Al | Pb | Bi | Se | | | | | | | |
| EM-BODIMENT | 1 | 64.5 | 33.631 | 0.009 | 0.06 | | | 1.8 | | | 65.2 | 6.7 | 1.80 | 33.6 | 3737 | 561 | α | α |
| | 2 | 65.7 | 33.322 | 0.008 | 0.07 | | | 0.9 | | | 65.9 | 8.8 | 0.90 | 33.3 | 4165 | 476 | α | α |
| | 3 | 62.5 | 34.411 | 0.009 | 0.08 | | | 3 | | | 63.8 | 8.9 | 3.00 | 34.4 | 3823 | 430 | α | α + β |
| | 4 | 61.3 | 37.217 | 0.013 | 0.07 | | | 1.4 | | | 61.8 | 5.4 | 1.40 | 37.2 | 2863 | 532 | α | α + β |
| | 5 | 61.3 | 37.217 | 0.013 | 0.07 | | | 1.4 | | | 61.8 | 5.4 | 1.40 | 37.2 | 2863 | 532 | α | α + β |
| | 6 | 61.4 | 35.93 | 0.01 | 0.06 | | | | 2.6 | | 62.5 | 6.0 | 2.60 | 35.9 | 3593 | 599 | α | α + β |
| | 7 | 71.4 | 27.14 | 0.01 | 0.05 | | | 1.4 | | | 72.10 | 5.0 | 1.40 | 27.1 | 2714 | 543 | α | α |
| | 8 | 64.7 | 34.413 | 0.017 | 0.07 | | | 0.8 | | | 64.9 | 4.1 | 0.80 | 34.4 | 2024 | 492 | α | α |
| | 9 | 63.4 | 34.991 | 0.009 | 0.07 | | | 1.4 | | 0.13 | 64.0 | 7.8 | 1.53 | 35.0 | 3888 | 500 | α | α |
| | 10 | 64 | 35.021 | 0.009 | 0.07 | | | 0.9 | | | 64.2 | 7.8 | 0.90 | 35.0 | 3891 | 500 | α | α |
| | 11 | 64.3 | 33.963 | 0.007 | 0.08 | | | 1.4 | | 0.25 | 64.9 | 11.4 | 1.65 | 34.0 | 4852 | 425 | α | α |
| | 12 | 64.1 | 34.284 | 0.016 | 0.1 | | | | 1.3 | 0.2 | 64.6 | 6.3 | 1.50 | 34.3 | 2143 | 343 | α | α |
| | 13 | 63.5 | 35.547 | 0.0034 | 0.05 | 1 | | 0.9 | | | 63.3 | 14.7 | 1.05 | 37.0 | 10896 | 741 | α | α + γ + β |
| | 14 | 63.5 | 34.635 | 0.0055 | 0.06 | 0.9 | | 0.9 | | | 63.3 | 10.9 | 1.00 | 36.9 | 6706 | 615 | α | α + γ |
| | 15 | 63.8 | 340222 | 0.0079 | 0.07 | 1 | | 0.9 | | | 63.5 | 8.9 | 1.05 | 36.7 | 4648 | 525 | α | α + γ |
| | 16 | 63.7 | 34.318 | 0.012 | 0.07 | 1 | | 0.9 | | | 63.4 | 5.8 | 1.05 | 36.8 | 3068 | 526 | α | α + γ |
| | 17 | 63.4 | 34.614 | 0.026 | 0.06 | 1 | | 0.9 | | | 63.2 | 2.3 | 1.05 | 37.1 | 1427 | 619 | α | α + γ + β |
| | 18 | 63.5 | 34.596 | 0.034 | 0.07 | 0.9 | | 0.9 | | | 63.3 | 2.1 | 1.00 | 36.8 | 1084 | 526 | α | α + γ + β |
| | 19 | 63.8 | 34.276 | 0.009 | 0.015 | 1 | | 0.9 | | | 63.7 | 1.7 | 1.00 | 36.8 | 4086 | 2452 | α | α + γ |
| | 20 | 63.5 | 34.665 | 0.01 | 0.025 | 0.9 | | 0.9 | | | 63.4 | 2.5 | 1.05 | 36.9 | 3692 | 1477 | α | α + γ |
| | 21 | 63.4 | 34.658 | 0.009 | 0.033 | 1 | | 0.9 | | | 63.3 | 3.7 | 1.00 | 37.2 | 4129 | 1126 | α | α + γ |
| | 22 | 63.7 | 34.246 | 0.009 | 0.045 | 1.1 | | 0.9 | | | 63.5 | 5.0 | 1.05 | 37.0 | 4111 | 822 | α | α + γ |
| | 23 | 63.7 | 34.216 | 0.014 | 0.17 | 1 | | 0.9 | | | 63.1 | 12.1 | 1.00 | 36.7 | 2623 | 216 | α | α + γ + β |
| | 24 | 61.5 | 34.232 | 0.008 | 0.06 | 0.8 | | 3.4 | | | 62.6 | 7.5 | 3.50 | 36.2 | 4529 | 604 | α | α + γ + β |
| | 25 | 64.4 | 32.921 | 0.009 | 0.07 | 0.8 | | 1.8 | | | 64.7 | 7.8 | 1.85 | 34.9 | 3880 | 499 | α | α + γ |
| | 26 | 65.7 | 35.521 | 0.009 | 0.07 | 0.8 | | 0.9 | | | 65.5 | 7.8 | 0.95 | 34.5 | 3836 | 493 | α | α + γ |
| | 27 | 65.3 | 32.532 | 0.008 | 0.06 | 1.2 | | 0.9 | | | 65.0 | 7.5 | 1.05 | 35.5 | 4442 | 592 | α | α + γ |
| | 28 | 64.3 | 32.422 | 0.088 | 0.07 | 2.3 | | 0.9 | | | 63.4 | 8.8 | 1.50 | 38.2 | 4772 | 545 | α | α + γ |

TABLE 2

| Casting No. | | Alloy Composition (mass %) | | | | | | | | | f1 | f2 | f3 | f4 | f5 | f6 | Primary Crystal | Metal Structure |
|---|---|---|---|---|---|---|---|---|---|---|---|---|---|---|---|---|---|---|
| | | Cu | Zn | Zr | P | Sn | Al | Pb | Bi | Se | | | | | | | | |
| EM-BODIMENT | 29 | 63.8 | 32.141 | 0.009 | 0.05 | 3.1 | | 0.9 | | | 62.6 | 5.6 | 1.90 | 39.9 | 4432 | 798 | α | α + γ |
| | 30 | 64.6 | 32.52 | 0.01 | 0.07 | 2.3 | | 0.5 | | | 63.5 | 7.0 | 1.10 | 38.3 | 3827 | 547 | α | α + γ |
| | 31 | 64.1 | 32.231 | 0.009 | 0.06 | 3.1 | | 0.5 | | | 62.6 | 6.7 | 1.50 | 40.0 | 4442 | 666 | α | α + γ |
| | 32 | 63 | 34.224 | 0.016 | 0.06 | 1.4 | | 1.3 | | | 62.8 | 3.8 | 1.65 | 37.7 | 2358 | 629 | α | α + γ |
| | 33 | 64 | 34.476 | 0.014 | 0.06 | 0.15 | | 1.3 | | | 64.4 | 4.3 | 1.30 | 34.9 | 2489 | 581 | α | α |
| | 34 | 64.1 | 34.018 | 0.012 | 0.07 | 0.4 | | 1.4 | | | 64.4 | 5.8 | 1.40 | 35.0 | 2918 | 500 | α | α |
| | 35 | 64.5 | 33.526 | 0.014 | 0.06 | 0.6 | | 1.3 | | | 64.7 | 4.3 | 1.33 | 35.0 | 2502 | 584 | α | α + γ |
| | 36 | 61.4 | 36.328 | 0.012 | 0.06 | 0.9 | | 1.3 | | | 61.4 | 5.0 | 1.50 | 38.6 | 3215 | 643 | α | α + γ + β |
| | 37 | 61.4 | 36.328 | 0.012 | 0.06 | 0.9 | | 1.3 | | | 61.4 | 5.0 | 1.35 | 38.6 | 3215 | 643 | α | α + γ + β |
| | 38 | 61.9 | 35.696 | 0.014 | 0.09 | 0.9 | | 1.4 | | | 61.9 | 6.4 | 1.60 | 37.9 | 2710 | 422 | α | α + γ + β |
| | 39 | 61.9 | 35.696 | 0.014 | 0.09 | 0.9 | | 1.4 | | | 61.9 | 6.4 | 1.45 | 37.9 | 2710 | 422 | α | α + γ |
| | 40 | 67 | 28.926 | 0.014 | 0.06 | 0.9 | | 3.1 | | | 67.9 | 4.3 | 3.15 | 31.2 | 2227 | 520 | α | α + γ |
| | 41 | 67.7 | 29.926 | 0.014 | 0.06 | 0.9 | | 1.4 | | | 67.8 | 4.3 | 1.45 | 32.2 | 2298 | 536 | α | α + γ |
| | 42 | 71 | 26.926 | 0.014 | 0.06 | 1 | | 1 | | | 70.8 | 4.3 | 1.05 | 29.4 | 2102 | 490 | α | α + γ |
| | 43 | 67.2 | 29.94 | 0.01 | 0.05 | 2.2 | | 0.6 | | | 66.3 | 5.0 | 1.10 | 35.4 | 3544 | 709 | α | α + γ |
| | 44 | 64 | 33.626 | 0.038 | 0.036 | 1 | | 1.3 | | | 64.0 | 0.9 | 1.45 | 36.1 | 951 | 1004 | α | α + γ |
| | 45 | 63.9 | 33.832 | 0.03 | 0.038 | 0.9 | | 1.3 | | | 64.0 | 1.3 | 1.40 | 36.1 | 1203 | 950 | α | α + γ |
| | 46 | 63.9 | 33.505 | 0.005 | 0.19 | 1.1 | | 1.3 | | | 63.4 | 38.0 | 1.45 | 36.3 | 7251 | 191 | α | α + γ + β |
| | 47 | 64 | 33.153 | 0.007 | 0.14 | 1.1 | | 1.4 | | | 63.7 | 20.0 | 1.55 | 36.1 | 5158 | 258 | α | α + γ |
| | 48 | 63 | 33.831 | 0.009 | 0.06 | 1 | 0.3 | 1.8 | | | 63.4 | 6.7 | 2.25 | 36.3 | 4037 | 606 | α | α + γ + β |
| | 49 | 62.2 | 34.631 | 0.009 | 0.06 | 1 | | | 2.1 | | 62.6 | 6.7 | 2.30 | 37.1 | 4126 | 619 | α | α + γ + β |
| | 50 | 63 | 34.041 | 0.009 | 0.05 | 0.9 | | 1.6 | | 0.4 | 63.4 | 5.6 | 2.15 | 36.3 | 4032 | 726 | α | α + γ + β |
| | 51 | 64.3 | 32.622 | 0.008 | 0.07 | 1.5 | | 1.2 | | 0.3 | 64.1 | 8.8 | 1.90 | 36.4 | 4547 | 520 | α | α + γ |
| | 52 | 64.5 | 32.621 | 0.009 | 0.07 | 2.3 | | 0.5 | | | 63.4 | 7.8 | 1.10 | 38.4 | 4263 | 548 | α | α + γ |
| | 53 | 65 | 30.821 | 0.009 | 0.07 | 1.5 | | | 2.6 | | 65.3 | 7.8 | 2.95 | 34.6 | 3841 | 494 | α | α + γ |
| | 54 | 63.5 | 34.432 | 0.008 | 0.06 | 1.2 | | | 0.8 | | 63.1 | 7.5 | 1.00 | 37.4 | 4679 | 624 | α | α + γ + β |
| | 55 | 63.8 | 32.551 | 0.009 | 0.1 | 2.8 | | | 0.7 | 0.4 | 62.5 | 11.1 | 1.64 | 39.6 | 4395 | 396 | α | α + γ |
| | 56 | 64.5 | 34.068 | 0.012 | 0.07 | | 0.15 | 1.2 | | | 64.6 | 5.8 | 1.20 | 34.5 | 2877 | 493 | α | α |

TABLE 3

| Casting No. | | Alloy Composition (mass %) | | | | | | | | | | | |
|---|---|---|---|---|---|---|---|---|---|---|---|---|---|
| | | Cu | Zn | Zr | P | Sn | Al | Pb | Bi | Se | As | Sb | Mn | Si |
| EMBODIMENT | 57 | 62.5 | 33.908 | 0.012 | 0.08 | | 0.4 | 3.1 | | | | | | |
| | 58 | 65.8 | 32.106 | 0.014 | 0.08 | | 0.8 | 1.2 | | | | | | |
| | 59 | 71 | 25.725 | 0.015 | 0.06 | | 2.5 | 0.7 | | | | | | |
| | 60 | 63.5 | 33.826 | 0.014 | 0.06 | | 0.3 | | 2.3 | | | | | |
| | 61 | 63 | 35.165 | 0.015 | 0.07 | | 0.25 | | 1.2 | 0.3 | | | | |
| | 62 | 63.8 | 34.14 | 0.01 | 0.07 | 1 | 0.08 | 0.9 | | | | | | |
| | 63 | 65.3 | 31.891 | 0.009 | 0.08 | 1.8 | 0.12 | 0.8 | | | | | | |
| | 64 | 64.5 | 32.071 | 0.009 | 0.07 | 2.3 | 0.35 | 0.7 | | | | | | |
| | 65 | 64.8 | 32.812 | 0.008 | 0.06 | 1 | 0.22 | 1.1 | | | | | | |
| | 66 | 64.5 | 32.721 | 0.009 | 0.07 | 0.8 | 0.6 | 1.3 | | | | | | |
| | 67 | 66.8 | 27.911 | 0.009 | 0.08 | 2.8 | 1.4 | 1 | | | | | | |
| | 68 | 62.3 | 35.526 | 0.014 | 0.06 | 1 | 0.2 | 0.9 | | | | | | |
| | 69 | 63.8 | 33.941 | 0.009 | 0.05 | 1 | 0.2 | 1 | | | | | | |
| | 70 | 63.4 | 33.222 | 0.008 | 0.07 | 0.8 | 0.2 | | 1.8 | 0.5 | | | | |
| | 71 | 63.7 | 33.321 | 0.009 | 0.07 | 1.8 | 0.2 | | 0.9 | | | | | |
| | 72 | 63.8 | 34.319 | 0.011 | 0.07 | 0.6 | 0.2 | | 1 | | | | | |
| | 73 | 64 | 35.577 | 0.013 | 0.06 | 1.2 | 0.2 | | 0.8 | 0.15 | | | | |
| | 74 | 64 | 33.429 | 0.011 | 0.08 | 0.8 | 0.08 | | 1.6 | | | | | |
| | 75 | 63.8 | 34.12 | 0.01 | 0.07 | 1 | | 1 | | | | | | |
| | 76 | 64.1 | 33.821 | 0.009 | 0.07 | 1 | | 1 | | | | | | |
| | 77 | 65.2 | 33.682 | 0.008 | 0.07 | | | 1 | | | | | 0.4 | |
| | 78 | 63.5 | 35.282 | 0.008 | 0.06 | | | 1.1 | | | 0.05 | | | |
| | 79 | 64.1 | 30.032 | 0.008 | 0.06 | | | 1.2 | | | | | 3.5 | 1.1 |
| | 80 | 65.8 | 25.511 | 0.009 | 0.08 | | | 2.3 | | | | | 4.7 | 1.6 |
| | 81 | 66.8 | 32.11 | 0.01 | 0.08 | | | 1 | | | | | | |

| Casting No. | | Alloy Composition (mass %) | | f1 | f2 | f3 | f4 | f5 | f6 | Primary Crystal | Metal Structure |
|---|---|---|---|---|---|---|---|---|---|---|---|
| | | Mg | Impurities | | | | | | | | |
| EMBODIMENT | 57 | | | 63.1 | 6.7 | 3.10 | 35.1 | 2926 | 439 | α | α + β |
| | 58 | | | 64.7 | 5.7 | 1.20 | 34.5 | 2465 | 431 | α | α |
| | 59 | | | 66.7 | 4.0 | 0.85 | 33.2 | 2215 | 554 | α | α + γ |
| | 60 | | | 63.9 | 4.3 | 2.30 | 34.7 | 2480 | 579 | α | α + β |
| | 61 | | | 63.1 | 4.7 | 1.50 | 35.9 | 2394 | 513 | α | α + β |
| | 62 | | | 63.4 | 7.0 | 1.05 | 36.9 | 36.88 | 527 | α | α + γ |
| | 63 | | | 64.3 | 8.9 | 1.30 | 36.8 | 4083 | 459 | α | α + γ |
| | 64 | | | 62.9 | 7.8 | 1.45 | 38.9 | 4319 | 555 | α | α + γ |
| | 65 | | | 64.3 | 7.5 | 1.20 | 36.0 | 4497 | 600 | α | α + γ |
| | 66 | | | 63.5 | 7.8 | 1.35 | 36.5 | 4.58 | 522 | α | α + γ + β |
| | 67 | | | 63.1 | 8.9 | 2.20 | 39.1 | 4346 | 489 | α | α + γ |
| | 68 | | | 61.7 | 4.3 | 1.05 | 38.6 | 2759 | 644 | α | α + γ + β |
| | 69 | | | 63.3 | 5.6 | 1.15 | 37.0 | 4116 | 741 | α | α + γ + β |
| | 70 | | | 63.6 | 8.8 | 2.35 | 35.8 | 4478 | 512 | α | α + γ + β |
| | 71 | | | 62.7 | 7.8 | 1.40 | 38.4 | 4269 | 549 | α | α + γ |
| | 72 | | | 63.4 | 6.4 | 1.03 | 36.4 | 3311 | 520 | α | α + γ + β |
| | 73 | | | 63.3 | 4.6 | 1.20 | 37.2 | 2860 | 620 | α | α + γ |
| | 74 | | | 64.0 | 7.3 | 1.65 | 35.7 | 3243 | 446 | α | α + γ |
| | 75 | | 0.008 0.02 | 63.6 | 7.0 | 1.10 | 36.6 | 3662 | 523 | α | α + γ |
| | 76 | | 0.003 0.005 | 63.9 | 7.8 | 1.05 | 36.3 | 4.36 | 519 | α | α + γ |
| | 77 | | | 65.5 | 8.8 | 1.00 | 33.7 | 4210 | 481 | α | α |
| | 78 | | | 63.8 | 7.5 | 1.10 | 35.3 | 4410 | 588 | α | α + β |
| | 79 | | | 64.2 | 7.5 | 1.20 | 30.0 | 3754 | 501 | α | α |
| | 80 | | | 65.8 | 8.9 | 2.35 | 25.5 | 2835 | 319 | α | α + γ |
| | 81 | 0.008 | | 67.1 | 8.0 | 1.00 | 32.1 | 3211 | 401 | α | α |

TABLE 4

| Casting No. | | Alloy Composition (mass %) | | | | | | | | | | | |
|---|---|---|---|---|---|---|---|---|---|---|---|---|---|
| | | Cu | Zn | Zr | P | Sn | Al | Pb | Bi | Se | As | Sb | Mn |
| EMBODIMENT | 82 | 63 | 34.143 | 0.007 | 0.05 | | | 0.8 | | | | 1.5 | |
| | 83 | 64.1 | 33.76 | 0.01 | 0.08 | 1 | | 1 | | | | 0.05 | |
| | 84 | 64 | 33.449 | 0.011 | 0.09 | 0.8 | | 1.6 | | | 0.02 | 0.03 | |
| | 85 | 64 | 34.637 | 0.013 | 0.1 | | 0.2 | 1 | | | | 0.05 | |
| | 86 | 64.2 | 33.413 | 0.007 | 0.08 | 1 | 0.2 | 1 | | | 0.1 | | |
| | 87 | 63.9 | 33.411 | 0.009 | 0.08 | 0.8 | 0.3 | 1.4 | | | | 0.1 | |
| | 88 | 63.3 | 34.477 | 0.013 | 0.08 | 0.8 | | 0.7 | | | | 0.5 | |
| | 89 | 62.8 | 32.51 | 0.01 | 0.08 | 0.8 | | | 2.3 | | | 1.2 | |
| | 90 | 63.8 | 34.286 | 0.014 | 0.05 | 0.8 | | 0.9 | | | | 0.15 | |

TABLE 4-continued

| | | | | | | | | | | | |
|---|---|---|---|---|---|---|---|---|---|---|---|
| 91 | 63.2 | 34.841 | 0.009 | 0.08 | 0.8 | | 1 | | | | |
| 92 | 64 | 33.942 | 0.008 | 0.05 | 0.8 | | 1.2 | | | | |
| 93 | 64.9 | 28.111 | 0.009 | 0.08 | | 0.4 | 1.3 | | | | 4 |
| 94 | 65.5 | 28.31 | 0.01 | 0.08 | | 0.7 | 1.6 | | | | 3 |
| 95 | 66.1 | 29.959 | 0.011 | 0.08 | 1.6 | | 0.9 | | | | 1.1 |
| 96 | 72 | 23.282 | 0.008 | 0.06 | 3.1 | | 0.7 | | | | 0.7 |
| 97 | 63.8 | 29.717 | 0.013 | 0.07 | 1.3 | | 1 | | | | 3.1 |
| 98 | 65 | 31.395 | 0.015 | 0.09 | | 0.6 | | 0.8 | | | 1.6 |
| 99 | 66.3 | 27.01 | 0.01 | 0.08 | | 1 | 1.4 | | | | 3.2 |
| 100 | 64.8 | 32.061 | 0.009 | 0.08 | 0.15 | 0.8 | 1.2 | | | | 0.7 |
| 101 | 63.9 | 32.222 | 0.018 | 0.11 | 0.6 | 0.3 | 1.1 | 0.2 | | | 1.2 |
| 102 | 63.9 | 34.131 | 0.009 | 0.08 | 0.6 | | 1.2 | | | | |
| 103 | 63 | 34.183 | 0.007 | 0.06 | | | 1.4 | | 0.05 | | 1 |
| 104 | 64 | 32.167 | 0.013 | 0.08 | | 0.5 | 1.4 | | | 0.04 | 1.4 |
| 105 | 63.2 | 33.33 | 0.02 | 0.09 | 0.6 | | 1.3 | | 0.06 | | 1.1 |
| 106 | 64.1 | 33.849 | 0.011 | 0.08 | 0.7 | | 1.2 | | 0.06 | | |
| 107 | 64.5 | 31.242 | 0.008 | 0.08 | 0.08 | 0.8 | 1.2 | | | 0.04 | 1.6 |

| Casting | | Alloy Composition (mass %) | | f1 | f2 | f3 | f4 | f5 | f6 | Primary | Metal |
|---|---|---|---|---|---|---|---|---|---|---|---|
| No. | | Si | Mg | | | | | | | crystal | Structure |
| EM-BODIMENT | 82 | 0.5 | | 63.0 | 7.1 | 0.80 | 34.1 | 4878 | 683 | α | α + β |
| | 83 | | | 63.8 | 8.0 | 1.10 | 36.3 | 3626 | 453 | α | α + γ |
| | 84 | | | 64.1 | 8.2 | 1.65 | 35.4 | 3223 | 394 | α | α + γ |
| | 85 | | | 63.8 | 7.7 | 1.00 | 35.2 | 2711 | 352 | α | α + γ + β |
| | 86 | | | 63.6 | 11.4 | 1.10 | 36.5 | 5216 | 456 | α | α + γ |
| | 87 | | | 63.4 | 8.9 | 1.45 | 36.3 | 4035 | 454 | α | α + γ + β |
| | 88 | 013 | | 63.1 | 6.2 | 0.75 | 36.5 | 2806 | 456 | α | α + γ + β |
| | 89 | 0.3 | | 63.5 | 8.0 | 2.40 | 34.5 | 3451 | 431 | α | α + γ + β |
| | 90 | | | 63.9 | 3.6 | 0.95 | 36.3 | 2592 | 726 | α | α + γ |
| | 91 | 0.07 | | 62.8 | 8.9 | 1.10 | 36.8 | 4093 | 461 | α | α + γ + β |
| | 92 | | 0.05 | 64.1 | 6.3 | 1.25 | 35.9 | 4493 | 719 | α | α + γ |
| | 93 | 1.2 | | 64.4 | 8.9 | 1.30 | 29.3 | 3257 | 366 | α | α |
| | 94 | 0.8 | | 65.0 | 8.0 | 1.60 | 30.4 | 3041 | 380 | α | α |
| | 95 | 0.25 | | 63.7 | 7.3 | 0.90 | 34.8 | 3160 | 434 | α | α + β |
| | 96 | 0.15 | | 66.8 | 7.5 | 0.90 | 34.8 | 4073 | 543 | α | α + γ |
| | 97 | 1 | | 61.4 | 5.4 | 1.00 | 33.6 | 2586 | 480 | α | α + β |
| | 98 | 0.5 | | 63.9 | 6.0 | 0.80 | 33.2 | 2213 | 369 | α | α |
| | 99 | 1 | | 64.7 | 8.0 | 1.40 | 30.0 | 3001 | 375 | α | α |
| | 100 | 0.2 | | 63.6 | 8.9 | 1.20 | 34.8 | 3871 | 435 | α | α |
| | 101 | 0.35 | | 63.4 | 6.1 | 1.30 | 34.6 | 1923 | 315 | α | α |
| | 102 | 0.08 | | 63.7 | 8.9 | 1.20 | 35.6 | 3959 | 445 | α | α |
| | 103 | 0.3 | | 63.4 | 8.6 | 1.40 | 34.2 | 4883 | 570 | α | α + β |
| | 104 | 0.4 | | 63.5 | 6.2 | 1.40 | 33.7 | 2590 | 421 | α | α + β |
| | 105 | 0.3 | | 63.3 | 4.5 | 1.35 | 34.8 | 1742 | 387 | α | α + γ + β |
| | 106 | | 0.005 | 64.1 | 7.3 | 1.25 | 35.6 | 3236 | 445 | α | α + γ |
| | 107 | 0.45 | | 63.4 | 1.0 | 1.20 | 33.8 | 4320 | 423 | α | α + β |

TABLE 5

| Casting | | Alloy Composition (mass %) | | | | | | | | | | |
|---|---|---|---|---|---|---|---|---|---|---|---|---|
| No. | | Cu | Zn | Zr | P | Sn | Al | Pb | Bi | Mn | Si | Impurities |
| COMPARATIVE EXAMPLE | 201 | 65.7 | 33.901 | 0.009 | 0.09 | | | 0.3 | | | | Fe Ni |
| | 202 | 65.7 | 34.216 | 0.009 | 0.07 | | | 0.005 | | | | |
| | 203 | 59.2 | 39.304 | 0.016 | 0.08 | | | 1.4 | | | | |
| | 204 | 63.5 | 34.55 | 0.0005 | 0.005 | 1 | | 0.9 | | | | |
| | 205 | 63.5 | 34.549 | 0.0012 | 0.05 | 1 | | 0.9 | | | | |
| | 206 | 63.8 | 34.176 | 0.054 | 0.07 | 1 | | 0.9 | | | | |
| | 207 | 63.4 | 34.52 | 0.09 | 0.09 | 1 | | 0.9 | | | | |
| | 208 | 63.3 | 34.784 | 0.009 | 0.007 | 1 | | 0.9 | | | | |
| | 209 | 64.2 | 33.6 | 0.01 | 0.29 | 1 | | 0.9 | | | | |
| | 210 | 60.5 | 36.22 | 0.01 | 0.07 | 2.3 | | 0.9 | | | | |
| | 211 | 64.3 | 29.925 | 0.015 | 0.06 | 4.4 | | 1.3 | | | | |
| | 212 | 59.3 | 38.506 | 0.014 | 0.08 | 0.9 | | 1.2 | | | | |
| | 213 | 63.8 | 33.835 | 0.045 | 0.02 | 1 | | 1.3 | | | | |
| | 214 | 64.1 | 33.369 | 0.0015 | 0.23 | 1 | | 1.3 | | | | |
| | 215 | 64 | 31.53 | 0.01 | 0.06 | 1.1 | | | | | 3.3 | |
| | 216 | 72 | 22.505 | 0.015 | 0.08 | | 4.2 | 1.2 | | | | |
| | 217 | 61.5 | 35.911 | 0.009 | 0.08 | 0.7 | 0.9 | 0.9 | | | | |
| | 218 | 60 | 34.009 | 0.011 | 0.08 | | | 0.9 | | 3.8 | 1.2 | |
| | 219 | 63.8 | 33.266 | 0.014 | 0.11 | 0.8 | 1.8 | | | | 0.21 | |

TABLE 5-continued

|  | 220 | 64.2 | 33.31 | 0.01 | 0.06 | 0.9 | 1.3 |  |  | 0.22 |
|  | 221 | 64.8 | 32.55 | 0.01 | 0.06 | 1 | 1.3 |  | 0.14 | 0.14 |
|  | 222 | 63.5 | 34.571 | 0.029 |  | 1 | 0.9 |  |  |  |

| | Casting No. | f1 | f2 | f3 | f4 | f5 | f6 | Primary Crystal | Metal Structure |
|---|---|---|---|---|---|---|---|---|---|
| COMPARATIVE EXAMPLE | 201 | 65.6 | 10.0 | 0.30 | 33.9 | 3767 | 377 | α | α |
|  | 202 | 65.5 | 7.8 | 0.01 | 34.2 | 3805 | 489 | α | α |
|  | 203 | 59.7 | 5.0 | 1.40 | 39.3 | 2457 | 491 | β | α + β |
|  | 204 | 63.3 | 100.0 | 1.05 | 37.0 | 74099 | 741 | α | α + γ + β |
|  | 205 | 63.3 | 41.7 | 1.05 | 37.0 | 30874 | 741 | α | α + γ + β |
|  | 206 | 63.5 | 1.3 | 1.00 | 36.7 | 679 | 524 | α | α + γ + β |
|  | 207 | 63.1 | 1.0 | 1.10 | 37.0 | 411 | 411 | α | α + γ + β |
|  | 208 | 63.2 | 0.8 | 1.05 | 37.3 | 4143 | 5326 | α | α + γ + β |
|  | 209 | 63.3 | 29.0 | 1.05 | 36.1 | 3610 | 123 | α | α + γ + β |
|  | 210 | 59.6 | 7.0 | 1.60 | 42.0 | 4197 | 600 | β | α + γ + β |
|  | 211 | 62.6 | 4.0 | 2.80 | 40.9 | 2728 | 682 | α | α + γ |
|  | 212 | 59.2 | 5.7 | 1.45 | 40.8 | 2911 | 509 | β | α + γ + β |
|  | 213 | 63.9 | 0.4 | 1.45 | 36.3 | 807 | 1817 | α | α + γ + β |
|  | 214 | 63.6 | 153.3 | 1.45 | 35.9 | 23912 | 156 | α | α + γ + β |
|  | 215 | 64.9 | 6.0 | 3.45 | 34.3 | 3428 | 571 | α | α + γ |
|  | 216 | 64.8 | 5.3 | 1.95 | 35.1 | 2340 | 439 | α | α + γ |
|  | 217 | 59.7 | 8.9 | 0.95 | 40.4 | 4485 | 505 | β | α + γ + β |
|  | 218 | 59.8 | 7.3 | 0.90 | 34.0 | 3092 | 425 | β | α + β |
|  | 219 | 64.0 | 7.9 | 1.80 | 35.3 | 2519 | 321 | α | α + γ + β |
|  | 220 | 64.2 | 6.0 | 1.30 | 35.6 | 3536 | 593 | α | α + γ + β |
|  | 221 | 64.8 | 6.0 | 1.35 | 35.1 | 3505 | 584 | α | α + γ |
|  | 222 | 63.5 | 0 | 0.90 | 37.1 | 1278 |  | α | α + γ + β |

TABLE 6

| | | Area Ratio (%) | | Mean Grain Size (μm) | Tatur Shrinkage Test | | | Maximum Corrosion Depth (μm) | Corrosion Loss (mg/cm$^2$) Erosion · corrosion test | | | | Machinability | |
|---|---|---|---|---|---|---|---|---|---|---|---|---|---|---|
| Casting No. | | α + γ | γ | | Castability | Grain Size | Casting Crack | | I | II | III | IV | Cutting Main component (N) | Chip Type |
| EMBODIMENT | 1 | 100 | 0 | 40 | ○ | ○ | ○ | 40 |  |  |  |  | 101 |  |
|  | 2 | 100 | 0 | 50 | ○ | ○ | ○ | 30 | 45 | 64 | 278 | 595 | 127 |  |
|  | 3 | 98 | 0 | 50 | ○ | ○ |  | 160 | 53 |  |  |  | 91 |  |
|  | 4 | 96 | 0 | 250 |  |  |  | 290 |  |  |  |  | 108 |  |
|  | 5 | 99 | 0 |  |  |  |  | 90 |  |  |  |  | 106 |  |
|  | 6 | 97 | 0 | 120 | Δ | Δ | Δ | 230 |  |  |  |  |  |  |
|  | 7 | 100 | 0 | 60 | ○ | ○ |  | 20 |  |  |  |  |  |  |
|  | 8 | 100 | 0 | 45 | ○ | ○ |  | 40 |  |  |  |  |  |  |
|  | 9 | 100 | 0 | 40 | ○ | ○ |  | 50 |  |  |  |  |  |  |
|  | 10 | 100 | 0 | 40 | ○ | ○ | ○ | 40 |  |  |  |  |  |  |
|  | 11 | 100 | 0 | 60 | ○ | ○ | ○ | 50 | 42 |  |  |  |  |  |
|  | 12 | 100 | 0 | 40 | ○ |  |  | 60 |  |  |  |  |  |  |
|  | 13 | 99 | 3 | 120 | ○ | ○ | ○ | 140 | 38 | 53 | 222 | 460 | 128 |  |
|  | 14 | 100 | 2 | 65 | ○ | ○ | ○ | 80 | 34 | 51 | 193 | 415 | 126 |  |
|  | 15 | 100 | 3 | 35 | ○ | ○ | ○ | 40 | 30 | 44 | 176 | 390 | 125 |  |
|  | 16 | 100 | 3 | 30 | ○ | ○ | ○ | 50 | 31 | 45 | 163 | 372 | 126 |  |
|  | 17 | 99 | 3 | 75 | ○ | ○ |  | 80 | 32 |  |  |  | 127 |  |
|  | 18 | 99 | 2 | 120 | Δ | ○ |  | 120 | 36 |  |  |  | 129 |  |
|  | 19 | 100 | 2 | 250 | Δ | Δ | Δ | 150 | 33 |  |  |  | 129 |  |
|  | 20 | 100 | 3 | 200 | Δ | Δ | Δ | 120 | 33 |  |  |  | 129 |  |
|  | 21 | 100 | 2 | 80 | ○ | ○ | ○ | 90 | 30 |  |  |  | 126 |  |
|  | 22 | 100 | 3 | 50 | ○ | ○ |  | 30 | 29 |  |  |  | 126 |  |
|  | 23 | 98 | 2 | 120 | Δ | ○ |  | 140 |  |  |  |  | 124 |  |
|  | 24 | 98 | 2 | 80 | ○ | ○ |  | 190 | 42 |  |  |  |  |  |
|  | 25 | 100 | 1 | 30 | ○ | ○ |  | 30 | 31 |  |  |  |  |  |
|  | 26 | 100 | 1 | 30 | ○ | ○ |  | 10 or less | 30 | 42 | 158 | 314 | 129 |  |
|  | 27 | 100 | 3 | 25 | ○ | ○ |  | 10 or less | 26 | 42 | 143 | 295 | 124 |  |
|  | 28 | 100 | 12 | 25 | ○ | ○ |  | 70 | 29 | 49 | 186 | 281 | 112 |  |

TABLE 6-continued

| | Casting No. | Tensile Strength (N/mm$^2$) | Proof Stress (N/mm$^2$) | Elongation (%) | Fatigue Strength (N/mm$^2$) | Cold Workability | Wear Loss (mg) | Semi-solid Metal castability |
|---|---|---|---|---|---|---|---|---|
| EMBODIMENT | 1 | | | | | ○ | | |
| | 2 | 312 | 103 | 26 | 110 | ○ | 430 | |
| | 3 | | | | | | | |
| | 4 | | | | | | | |
| | 5 | | | | | | | |
| | 6 | | | | | Δ | | |
| | 7 | | | | | | | |
| | 8 | | | | | | | ○ |
| | 9 | | | | | | | |
| | 10 | | | | | ○ | | |
| | 11 | | | | | ○ | | |
| | 12 | | | | | | | |
| | 13 | 305 | 109 | 23 | 116 | ○ | | Δ |
| | 14 | 316 | 128 | 25 | 135 | | | |
| | 15 | 331 | 135 | 24 | 142 | ○ | 210 | ○ |
| | 16 | 328 | 139 | 25 | 146 | ○ | | ○ |
| | 17 | 310 | 115 | 24 | | | | |
| | 18 | 306 | 112 | 22 | 121 | | | Δ |
| | 19 | 290 | 101 | 20 | | Δ | | X |
| | 20 | 299 | 108 | 21 | 113 | Δ | | |
| | 21 | 308 | 119 | 22 | | ○ | | |
| | 22 | 324 | 136 | 24 | 143 | | | |
| | 23 | 302 | 103 | 13 | | Δ | | |
| | 24 | | | | | | | |
| | 25 | | | | | | | |
| | 26 | 338 | 137 | 26 | 142 | | | |
| | 27 | 349 | 152 | 22 | 165 | | 195 | |
| | 28 | 334 | 165 | 16 | 172 | | 164 | |

TABLE 7

| | Casting No. | Area Ratio (%) α+γ | Area Ratio (%) γ | Mean Grain Size (μm) | Tatur Shrinkage Test Castability | Tatur Shrinkage Test Grain Size | Casting Crack | Maximum Corrosion Depth (μm) | Corrosion Loss (mg/cm$^2$) Erosion · corrosion test I | II | III | IV | Machinability Cutting Main component (N) | Chip Type |
|---|---|---|---|---|---|---|---|---|---|---|---|---|---|---|
| EMBODIMENT | 29 | 100 | 20 | 40 | Δ | ○ | Δ | 100 | 32 | | | | 105 | a |
| | 30 | 100 | 12 | 25 | ○ | ○ | ○ | 50 | 28 | 42 | 182 | 276 | 126 | a |
| | 31 | 100 | 20 | 30 | ○ | ○ | | 80 | 28 | | | | 120 | a |
| | 32 | 100 | 7 | 30 | ○ | ○ | | 30 | 26 | | | | | |
| | 33 | 100 | 0 | 40 | ○ | ○ | | 60 | 37 | | | | | |
| | 34 | 100 | 0 | 35 | ○ | ○ | | 50 | 36 | | | | | |
| | 35 | 100 | 0.5 | 30 | ○ | ○ | | 40 | 34 | | | | | |
| | 36 | 96 | 4 | 200 | Δ | Δ | | 280 | 56 | | | | | |
| | 37 | 99 | 1 | | | | | 80 | 35 | | | | | |
| | 38 | 97 | 4 | 150 | Δ | Δ | | 200 | 44 | 65 | 256 | 545 | | |
| | 39 | 100 | 1 | | | | | 40 | 32 | 49 | 176 | 406 | | |
| | 40 | 100 | 1 | 35 | Δ | ○ | Δ | 10 or less | | | | | | |
| | 41 | 100 | 1 | 35 | ○ | ○ | | 10 or less | | | | | | |
| | 42 | 100 | 1 | 35 | ○ | ○ | | 20 | 29 | | | | | |
| | 43 | 100 | 10 | 25 | ○ | ○ | ○ | 10 or less | 23 | 39 | 141 | 255 | 125 | a |
| | 44 | 100 | 3 | 200 | Δ | Δ | Δ | 120 | | | | | 116 | a |
| | 45 | 100 | 2 | 120 | Δ | Δ | | 80 | | | | | 113 | a |
| | 46 | 99 | 3 | 250 | Δ | Δ | | 220 | 41 | | | | 114 | a |
| | 47 | 100 | 3 | 120 | Δ | ○ | | 60 | 31 | | | | | |
| | 48 | 99 | 3 | 30 | ○ | ○ | | 80 | 33 | | | | | |
| | 49 | 98 | 4 | 40 | ○ | ○ | | 160 | 39 | | | | | |
| | 50 | 99 | 3 | 35 | ○ | ○ | | 90 | 33 | | | | 99 | a |
| | 51 | 100 | 8 | 25 | ○ | ○ | ○ | 10 or less | 24 | 41 | 145 | 263 | 101 | a |
| | 52 | 100 | 12 | 25 | ○ | ○ | | 40 | 24 | 43 | 148 | 254 | 130 | a |
| | 53 | 100 | 7 | 30 | Δ | ○ | Δ | 20 | 23 | | | | 94 | c |
| | 54 | 99 | 4 | 30 | ○ | ○ | ○ | 90 | 30 | | | | 129 | a |
| | 55 | 100 | 18 | 35 | ○ | ○ | | 30 | 24 | 43 | 152 | 243 | 110 | a |
| | 56 | 100 | 0 | 30 | ○ | ○ | | 40 | 38 | | | | | |

TABLE 7-continued

| | Casting No. | Tensile Strength (N/mm$^2$) | Proof Stress (N/mm$^2$) | Elongation (%) | Fatigue Strength (N/mm$^2$) | Cold Workability | Wear Loss (mg) | Semi-solid Metal castability |
|---|---|---|---|---|---|---|---|---|
| EMBODIMENT | 29 | | | | | Δ | | |
| | 30 | 336 | 166 | 18 | 171 | | 162 | |
| | 31 | | | | | | | |
| | 32 | | | | | | | |
| | 33 | 322 | 112 | 26 | | | | |
| | 34 | | | | | | | |
| | 35 | | | | | | | |
| | 36 | | | | | | | |
| | 37 | | | | | | | |
| | 38 | | | | | | | |
| | 39 | | | | | | | |
| | 40 | | | | | | | |
| | 41 | | | | | | | |
| | 42 | | | | | | | ○ |
| | 43 | 340 | 166 | 19 | 175 | ○ | 155 | |
| | 44 | 298 | 107 | 19 | 112 | | | |
| | 45 | | | | | | | |
| | 46 | 290 | 103 | 18 | | | | |
| | 47 | | | | | | | |
| | 48 | | | | | | | |
| | 49 | | | | | | | |
| | 50 | | | | | | | |
| | 51 | 348 | 151 | 17 | | | | |
| | 52 | | | | | | | ○ |
| | 53 | | | | | Δ | | |
| | 54 | 341 | 144 | 20 | | ○ | | |
| | 55 | | | | | | | |
| | 56 | | | | | | | |

TABLE 8

| | Casting No. | Area Ratio (%) α+γ | Area Ratio (%) γ | Mean Grain Size (μm) | Tatur Shrinkage Test Castability | Tatur Shrinkage Test Grain Size | Casting Crack | Maximum Corrosion Depth (μm) | Corrosion Loss (mg/cm$^2$) Erosion·corrosion test I | II | III | IV | Machinability Cutting Main component (N) | Chip Type |
|---|---|---|---|---|---|---|---|---|---|---|---|---|---|---|
| EMBODIMENT | 57 | 98 | 0 | 35 | ○ | ○ | | 160 | 41 | | | | 121 | a |
| | 58 | 100 | 0 | 30 | ○ | ○ | ○ | 50 | 35 | 56 | 192 | 435 | | |
| | 59 | 100 | 3 | 45 | ○ | ○ | | 30 | 29 | 50 | 159 | 310 | 143 | e |
| | 60 | 99 | 0 | 35 | ○ | ○ | | 80 | | | | | | |
| | 61 | 99 | 0 | 35 | ○ | ○ | ○ | 90 | | | | | | |
| | 62 | 100 | 3 | 30 | ○ | ○ | ○ | 40 | 31 | | | | 130 | a |
| | 63 | 100 | 10 | 25 | ○ | ○ | ○ | 10 or less | 22 | 39 | 141 | 223 | 124 | a |
| | 64 | 100 | 15 | 30 | ○ | ○ | | 50 | 27 | 43 | 148 | 247 | 119 | a |
| | 65 | 100 | 2 | 25 | ○ | ○ | | 10 or less | 25 | 42 | 151 | 266 | 124 | a |
| | 66 | 99 | 1 | 30 | ○ | ○ | | 70 | 31 | | | | 117 | a |
| | 67 | 100 | 24 | 40 | Δ | ○ | Δ | 60 | 25 | | | | | |
| | 68 | 97 | 3 | 200 | Δ | Δ | | 280 | 48 | | | | | |
| | 69 | 99 | 3 | 30 | ○ | ○ | | 90 | 33 | | | | | |
| | 70 | 99 | 1 | 25 | ○ | ○ | | 70 | 33 | | | | 97 | c |
| | 71 | 100 | 10 | 35 | ○ | ○ | | 50 | 29 | 45 | 155 | 253 | 120 | a |
| | 72 | 99 | 0.5 | 35 | ○ | ○ | | 100 | 36 | | | | | |
| | 73 | 100 | 5 | 35 | ○ | ○ | | 60 | 30 | | | | 124 | a |
| | 74 | 100 | 1 | 30 | ○ | ○ | | 50 | 32 | 49 | 177 | 435 | 106 | a |
| | 75 | 100 | 2 | 60 | ○ | ○ | | 50 | | | | | | |
| | 76 | 100 | 1 | 70 | ○ | ○ | | 50 | 35 | 49 | 185 | 404 | 129 | a |
| | 77 | 100 | 0 | 45 | ○ | ○ | | 40 | | | | | | |
| | 78 | 99 | 0 | 50 | ○ | ○ | | 70 | | | | | | |
| | 79 | 100 | 0 | 40 | ○ | ○ | | 80 | 41 | 64 | 255 | 305 | 125 | a |
| | 80 | 100 | 1 | 30 | ○ | ○ | | 60 | | | | | | |
| | 81 | 100 | 0 | 45 | ○ | ○ | | 30 | | | | | | |

TABLE 8-continued

| | Casting No. | Tensile Strength (N/mm²) | Proof Stress (N/mm²) | Elongation (%) | Fatigue Strength (N/mm²) | Cold Workability | Wear Loss (mg) | Semi-solid Metal castability |
|---|---|---|---|---|---|---|---|---|
| EMBODIMENT | 57 | 322 | 117 | 27 | 122 | | | |
| | 58 | 330 | 139 | 26 | 145 | ○ | 220 | ○ |
| | 59 | 356 | 153 | 23 | 163 | | 145 | |
| | 60 | | | | | | | |
| | 61 | | | | | ○ | | |
| | 62 | | | | | ○ | | |
| | 63 | 345 | 152 | 21 | 164 | | 185 | |
| | 64 | 342 | 165 | 18 | 178 | | 150 | |
| | 65 | 345 | 138 | 27 | 146 | | | |
| | 66 | | | | | | | |
| | 67 | | | | | | | |
| | 68 | | | | | | | |
| | 69 | | | | | | | |
| | 70 | 342 | 136 | 27 | 146 | | 205 | |
| | 71 | 340 | 132 | 20 | 140 | | | |
| | 72 | | | | | | | |
| | 73 | 338 | 134 | 22 | 145 | | | |
| | 74 | 342 | 132 | 25 | | | | |
| | 75 | | | | | | | |
| | 76 | 324 | 123 | 22 | 133 | | | |
| | 77 | | | | | | | |
| | 78 | | | | | | | |
| | 79 | 384 | 156 | 20 | 166 | | 4.7 | |
| | 80 | | | | | | | |
| | 81 | | | | | | | |

TABLE 9

| | Casting No. | Area Ratio (%) α + γ | Area Ratio (%) γ | Mean Grain Size (μm) | Tatur Shrinkage Test Castability | Tatur Shrinkage Test Grain Size | Maximum Corrosion Depth (μm) | Corrosion Loss (mg/cm²) Erosion · corrosion test I | II | III | IV | Machinability Cutting Main component (N) | Chip Type |
|---|---|---|---|---|---|---|---|---|---|---|---|---|---|
| EMBODIMENT | 82 | 99 | 0 | 50 | ○ | ○ | 100 | | | | | 140 | a |
| | 83 | 100 | 2 | 35 | ○ | ○ | 30 | 30 | | | | | |
| | 84 | 100 | 1 | 30 | ○ | ○ | 30 | 31 | | | | | |
| | 85 | 99 | 0 | 40 | ○ | ○ | 80 | 40 | | | | | |
| | 86 | 100 | 2 | 40 | ○ | ○ | 40 | 31 | | | | | |
| | 87 | 99 | 1 | 35 | ○ | ○ | 90 | 35 | 51 | 198 | 402 | 110 | a |
| | 88 | 99 | 1 | 30 | ○ | ○ | 80 | 35 | 50 | 192 | 365 | 138 | a |
| | 89 | 99 | 2 | 40 | ○ | ○ | 80 | 35 | 49 | 187 | 312 | 100 | a |
| | 90 | 100 | 1 | 35 | ○ | ○ | 30 | 31 | | | | | |
| | 91 | 99 | 2 | 35 | ○ | ○ | 100 | | | | | | |
| | 92 | 100 | 1 | 25 | ○ | ○ | 30 | 30 | | | | | |
| | 93 | 100 | 0 | 40 | ○ | ○ | 40 | | | | | | |
| | 94 | 100 | 0 | 30 | ○ | ○ | 50 | 34 | 53 | 204 | 296 | 115 | a |
| | 95 | 99 | 0 | 35 | ○ | ○ | 90 | 42 | 55 | 193 | 275 | 136 | e |
| | 96 | 100 | 4 | 60 | ○ | ○ | 40 | 30 | 47 | 190 | 253 | 141 | a |
| | 97 | 95 | 0 | 200 | Δ | Δ | 300 | | | | | | |
| | 98 | 100 | 0 | 40 | ○ | ○ | 60 | | | | | 141 | e |
| | 99 | 100 | 0 | 40 | ○ | ○ | 40 | | | | | | |
| | 100 | 100 | 0 | 35 | ○ | ○ | 50 | | | | | | |
| | 101 | 100 | 0 | 40 | ○ | ○ | 40 | 31 | 48 | 194 | 268 | 124 | a |
| | 102 | 100 | 0 | 35 | ○ | ○ | 40 | | | | | | |
| | 103 | 99 | 0 | 40 | ○ | ○ | 80 | 40 | | | | | |
| | 104 | 99 | 0 | 45 | ○ | ○ | 90 | | | | | | |
| | 105 | 99 | 1 | 40 | ○ | ○ | 70 | 36 | | | | | |
| | 106 | 100 | 1 | 30 | ○ | ○ | 30 | | | | | | |
| | 107 | 98 | 0 | 40 | ○ | ○ | 140 | | | | | | |

| | Casting No. | Tensile Strength (N/mm²) | Proof Stress (N/mm²) | Elongation (%) | Fatigue Strength (N/mm²) | Wear Loss (mg) |
|---|---|---|---|---|---|---|
| EMBODIMENT | 82 | 356 | 143 | 22 | 149 | 24 |
| | 83 | | | | | |
| | 84 | | | | | |
| | 85 | | | | | |
| | 86 | | | | | |

TABLE 9-continued

| | | | | | |
|---|---|---|---|---|---|
| 87 | 338 | 125 | 26 | | |
| 88 | 350 | 135 | 23 | 145 | 54 |
| 89 | | | | | 32 |
| 90 | | | | | |
| 91 | | | | | |
| 92 | | | | | |
| 93 | | | | | |
| 94 | 436 | 168 | 20 | 182 | 3 |
| 95 | 408 | 157 | 21 | 170 | 18 |
| 96 | | | | | |
| 97 | | | | | |
| 98 | 380 | 152 | 20 | 162 | 26 |
| 99 | | | | | |
| 100 | | | | | |
| 101 | 362 | 148 | 20 | 155 | 36 |
| 102 | | | | | |
| 103 | | | | | |
| 104 | | | | | |
| 105 | | | | | |
| 106 | | | | | |
| 107 | | | | | |

TABLE 10

| | Casting No. | Area Ratio (%) α + γ | Area Ratio (%) γ | Mean Grain Size (μm) | Tatur Shrinkage Test Castability | Tatur Shrinkage Test Grain Size | Casting Crack | Maximum Corrosion Depth (μm) | Corrosion Loss (mg/cm²) Erosion · corrosion test I | II | III | IV | Machinability Cutting Main component (N) | Chip Type |
|---|---|---|---|---|---|---|---|---|---|---|---|---|---|---|
| COMPARATIVE EXAMPLE | 201 | 100 | 0 | 40 | ○ | ○ | | 30 | | | | | 183 | G |
| | 202 | 100 | 0 | 40 | ○ | ○ | | 40 | | | | | 258 | G |
| | 203 | 86 | 0 | 500 | Δ | X | | 900 | 65 | 119 | 430 | 850 | 108 | A |
| | 204 | 97 | 3 | 1000 | X | X | X | 400 | 50 | 74 | 323 | 588 | 134 | E |
| | 205 | 98 | 3 | 250 | Δ | X | X | 220 | 42 | 61 | 265 | 504 | 128 | E |
| | 206 | 99 | 2 | 350 | X | X | X | 190 | 41 | | | | 132 | E |
| | 207 | 99 | 4 | 400 | X | X | X | 230 | 43 | 60 | 260 | 480 | 134 | E |
| | 208 | 98 | 3 | 800 | X | X | X | 350 | 48 | | | | 133 | E |
| | 209 | 98 | 3 | 150 | X | Δ | X | 230 | | | | | 128 | a |
| | 210 | 95 | 14 | 350 | Δ | X | | 500 | 54 | | | | | |
| | 211 | 100 | 30 | 50 | X | ○ | X | 120 | 31 | | | | | |
| | 212 | 84 | 5 | 700 | Δ | X | | 750 | 61 | | | | | |
| | 213 | 99 | 3 | 500 | X | X | X | 260 | 45 | | | | 120 | A |
| | 214 | 99 | 3 | 800 | X | X | | 320 | 48 | | | | 124 | a |
| | 215 | 100 | 3 | 30 | X | ○ | X | 40 | 33 | | | | | |
| | 216 | 100 | 15 | 120 | X | Δ | | 80 | | | | | | |
| | 217 | 85 | 1 | 800 | Δ | X | | 600 | 59 | | | | | |
| | 218 | 88 | 0 | 500 | Δ | X | | 800 | | | | | | |
| | 219 | 99 | 0 | 500 | X | X | X | 320 | 59 | 74 | 338 | 595 | 105 | a |
| | 220 | 99 | 0 | 550 | X | X | X | 280 | 52 | | | | | |
| | 221 | 100 | 1 | 550 | X | X | X | | | | | | | |
| | 222 | 98 | 2 | 450 | X | X | X | 300 | 46 | | | | 134 | e |

| | Casting No. | Tensile Strength (N/mm²) | Proof Stress (N/mm²) | Elongation (%) | Fatigue Strength (N/mm²) | Cold Workability | Wear Loss (mg) | Semi-solid Metal castability |
|---|---|---|---|---|---|---|---|---|
| COMPARATIVE EXAMPLE | 201 | | | | | | | |
| | 202 | | | | | | | |
| | 203 | 285 | 86 | 16 | 87 | 550 | | X |
| | 204 | 261 | 90 | 19 | 91 | 320 | X | X |
| | 205 | 298 | 106 | 22 | | | | Δ |
| | 206 | 288 | 95 | 21 | | | | |
| | 207 | 278 | 94 | 18 | 96 | | | |
| | 208 | 258 | 91 | 20 | 94 | 345 | | |
| | 209 | 294 | 105 | 9 | 98 | | X | |
| | 210 | 294 | 92 | 8 | 91 | | X | |
| | 211 | | | | | | X | |
| | 212 | 286 | 90 | 12 | 89 | | | |
| | 213 | 278 | 92 | 19 | 92 | | | |
| | 214 | 262 | 93 | 16 | 89 | | | |
| | 215 | | | | | | | |
| | 216 | | | | | | | |
| | 217 | | | | | | | X |

TABLE 10-continued

| 218 | | | | | | |
|---|---|---|---|---|---|---|
| 219 | 268 | 93 | 20 | 98 | Δ | X |
| 220 | | | | | | |
| 221 | | | | | Δ | |
| 222 | 268 | 92 | 17 | 93 | | X |

The invention claimed is:

1. A copper alloy casting containing:
Cu: 58 to 72.5 mass %; Zr: 0.0008 to 0.045 mass %; P: 0.01 to 0.25 mass %; one or more elements selected from Pb: 0.01 to 4 mass %, Bi: 0.01 to 3 mass %, Se: 0.03 to 1 mass %, and Te: 0.05 to 1.2 mass %; and Zn: a remainder,
wherein the copper alloy casting satisfies the following equations, f1=[Cu]−3[P]+0.5([Pb]+[Bi]+[Se]+[Te])=60 to 90, f2=[P]/[Zr]=0.5 to 120, and f3=0.05[γ]+([Pb]+[Bi]+[Se]+[Te])=0.45 to 4, wherein the content of each element 'a' is denoted as [a] mass %, the content of γ phase is denoted as [γ]% by area ratio, and each element 'a' that is not contained in the copper alloy casting is denoted as [a]=0;
wherein the copper alloy casting forms a phase structure in which the total content of α phase and γ phase is 85% or more by area ratio and the content of the γ phase is 25% or less by area ratio; and
wherein the copper alloy casting has a mean grain size of 250 μm or less in a macrostructure at melt-solidification, and wherein the copper alloy casting has a shape determined by a mold.

2. The copper alloy casting according to claim 1, wherein when the copper alloy casting contains 0.0079 mass % of Zr, the copper alloy casting has a mean grain size of 35 μm in a macrostructure at melt-solidification.

3. The copper alloy casting according to claim 1, wherein when the copper alloy casting satisfies f2=8.9, the copper alloy casting has a mean grain size of 35 μm in a macrostructure at melt-solidification.

4. A copper alloy casting containing:
Cu: 58 to 72.5 mass %; Zr: 0.0008 to 0.045 mass %; P: 0.01 to 0.25 mass %; one or more elements selected from Pb: 0.01 to 4 mass %, Bi: 0.01 to 3 mass %, Se: 0.03 to 1 mass %, and Te: 0.05 to 1.2 mass %; Sn: 0.05 to 4 mass % and/or Al: 0.01 to 4 mass %; and Zn: a remainder,
wherein the copper alloy casting satisfies the following equations, f1=[Cu]−3[P]+0.5([Pb]+[Bi]+[Se]+[Te])−0.5[Sn]−1.8[Al]=60 to 90, f2=[P]/[Zr]=0.5 to 120, f3=0.05[γ]+([Pb]+[Bi]+[Se]+[Te])=0.45 to 4, f4=[Zn]+2.5[Sn]+3[Al]=15 to 42, f5=([Zn]+2.5[Sn]+3[Al])/[Zr]= 500 to 20000, and f6=([Zn]+2.5[Sn]+3[Al])/[P]= 75 to 3000, wherein the content of each element 'a' is denoted as [a] mass %, the content of γ phase is denoted as [γ]% by area ratio, and each element 'a' that is not contained in the copper alloy casting is denoted as [a]=0;
wherein the copper alloy casting forms a phase structure in which the total content of α phase and γ phase is 85% or more by area ratio and the content of γ phase is 25% or less by area ratio; and
wherein the copper alloy casting has a mean grain size of 250 μm or less in a macrostructure at melt-solidification, and wherein the copper alloy casting has a shape determined by a mold.

5. A copper alloy casting containing:
Cu: 58 to 72.5 mass %; Zr: 0.0008 to 0.045 mass %; P: 0.01 to 0.25 mass %; one or more elements selected from Pb: 0.01 to 4 mass %, Bi: 0.01 to 3 mass %, Se: 0.03 to 1 mass %, and Te: 0.05 to 1.2 mass %; As: 0.02 to 0.2 mass % and/or Sb: 0.02 to 0.2 mass %; and Zn: a remainder,
wherein the copper alloy casting satisfies the following equations, f1=[Cu]−3[P]+0.5([Pb]+[Bi]+[Se]+[Te])−([As]+[Sb])=60 to 90, f2=[P]/[Zr]=0.5 to 120, and f3=0.05[γ]+([Pb]+[Bi]+[Se]+[Te])=0.45 to 4, the content of each element 'a' is denoted as [a] mass %, the content of γ phase is denoted as [γ]% by area ratio, and each element 'a' that is not contained in the copper alloy casting is denoted as [a]=0;
wherein the copper alloy casting forms a phase structure in which the total content of α phase and γ phase is 85% or more by area ratio and the content of γ-phase is 25% or less by area ratio; and
wherein the copper alloy casting has a mean grain size of 250 μm or less in a macrostructure at melt-solidification, and wherein the copper alloy casting has a shape determined by a mold.

6. A copper alloy casting containing:
Cu: 58 to 72.5 mass %; Zr: 0.0008 to 0.045 mass %; P: 0.01 to 0.25 mass %; one or more elements selected from Pb: 0.01 to 4 mass %, Bi: 0.01 to 3 mass %, Se: 0.03 to 1 mass %, and Te: 0.05 to 1.2 mass %; one or more elements selected from Mn: 0.1 to 5 mass %, Si: 0.05 to 2 mass %, and Mg: 0.001 to 0.2 mass %; and Zn: a remainder,
wherein the copper alloy casting satisfies the following equations, f1=[Cu]−3[P]+0.5([Pb]+[Bi]+[Se]+[Te])+[Mn]−3.5[Si]−0.5[Mg]=60 to 90, f2=[P]/[Zr]=0.5 to 120, and f3=0.05[γ]+([Pb]+[Bi]+[Se]+[Te])=0.45 to 4, wherein the content of each element 'a' is denoted as [a] mass %, the content of γ phase is denoted as [γ]% by area ratio, and each element 'a' that is not contained in the copper alloy casting is denoted as [a]=0;
wherein the copper alloy casting forms a phase structure in which the total content of α phase and γ phase is 85% or more by area ratio and the content of γ-phase is 25% or less by area ratio; and
wherein the copper alloy casting has a mean grain size of 250 μM or less in a macrostructure at melt-solidification, and wherein the copper alloy casting has a shape determined by a mold.

7. A copper alloy casting containing:
Cu: 58 to 72.5 mass %; Zr: 0.0008 to 0.045 mass %; P: 0.01 to 0.25 mass %; one or more elements selected from Pb: 0.01 to 4 mass %, Bi: 0.01 to 3 mass %, Se: 0.03 to 1 mass %, and Te: 0.05 to 1.2 mass %; Sn: 0.05 to 4 mass % and/or Al: 0.01 to 4 mass %; As: 0.02 to 0.2 mass % and/or Sb: 0.02 to 0.2 mass %; and Zn: a remainder,
wherein the copper alloy casting satisfies the following equations, f1=[Cu]−3[P]+0.5([Pb]+[Bi]+[Se]+[Te])−0.5[Sn]−1.8[Al]−([As]+[Sb])=60 to 90, f2=[P]/[Zr]

=0.5 to 120, f3=0.05[γ]+([Pb]+[Bi]+[Se]+[Te])=0.45 to 4, f4=[Zn]+2.5[Sn]+3[Al]=15 to 42, f5=([Zn]+2.5[Sn]+3[Al])/[Zr]=500 to 20000, and f6=([Zn]+2.5 [Sn]+3 [Al])/[P]=75 to 3000, wherein the content of each element 'a' is denoted as [a] mass %, the content of γ-phase is denoted as [γ]% by area ratio, and each element 'a' that is not contained in the copper alloy casting is denoted as [a]=0;

wherein the copper alloy casting forms a phase structure in which the total content of α phase and γ phase is 85% or more by area ratio and the content of γ phase is 25% or less by area ratio; and wherein the copper alloy casting has a mean grain size of 250 μm or less in a macrostructure at melt-solidification, and wherein the copper alloy casting has a shape determined by a mold.

8. A copper alloy casting containing:

Cu: 58 to 72.5 mass %; Zr: 0.0008 to 0.045 mass %; P: 0.01 to 0.25 mass %; one or more elements selected from Pb: 0.01 to 4 mass %, Bi: 0.01 to 3 mass %, Se: 0.03 to 1 mass %, and Te: 0.05 to 1.2 mass %; Sn: 0.05 to 4 mass % and/or Al: 0.01 to 4 mass %; one or more elements selected from Mn: 0.1 to 5 mass %, Si: 0.05 to 2 mass %, and Mg: 0.001 to 0.2 mass %; and Zn: a remainder, wherein the copper alloy casting satisfies the following equations, f1=[Cu]−3[P]+0.5([Pb]+[Bi]+[Se]+[Te])−0.5[Sn]−1.8[Al]+[Mn]−3.5[Si]−0.5[Mg]=60 to 90, f2=[P]/[Zr]=0.5 to 120, f3=0.05[γ]+([Pb]+[Bi]+[Se]+[Te])= 0.45 to 4, f4=[Zn]+2.5[Sn]+3[Al]=15 to 42, f5=([Zn]+2.5[Sn]+3[Al])/[Zr]=500 to 20000, and f6=([Zn]+2.5[Sn]+3[Al])/[P]=75 to 3000, wherein the content of each element 'a' is denoted as [a] mass %, the content of γ phase is denoted as [γ]% by area ratio, and each element 'a' that is not contained in the copper alloy casting is denoted as [a]=0;

wherein the copper alloy casting forms a phase structure in which the total content of α phase and γ phase is 85% or more by area ratio and the content of γ phase is 25% or less by area ratio; and wherein the copper alloy casting has a mean grain size of 250 μm or less in a macrostructure at melt-solidification, and wherein the copper alloy casting has a shape determined by a mold.

9. A copper alloy casting containing:

Cu: 58 to 72.5 mass %; Zr: 0.0008 to 0.045 mass %; P: 0.01 to 0.25 mass %; one or more elements selected from Pb: 0.01 to 4 mass %, Bi: 0.01 to 3 mass %, Se: 0.03 to 1 mass %, and Te: 0.05 to 1.2 mass %; As: 0.02 to 0.2 mass % and/or Sb: 0.02 to 0.2 mass %; and one or more elements selected from Mn: 0.1 to 5 mass %, Si: 0.05 to 2 mass %, Mg: 0.001 to 0.2 mass %; and Zn: a remainder, wherein the copper alloy casting satisfies the following equations, f1=[Cu]−3[P]+0.5([Pb]+[Bi]+[Se]+[Te])−([As]+[Sb])+[Mn]−3.5[Si]−0.5[Mg]=60 to 90, f2=[P]/[Zr]=0.5 to 120, and f3=0.05[γ]+([Pb]+[Bi]+[Se]+[Te])= 0.45 to 4, wherein the content of each element 'a' is denoted as [a] mass %, the content of γ phase is denoted as [γ]% by area ratio, and each element 'a' that is not contained in the copper alloy casting is denoted as [a]=0;

wherein the copper alloy casting forms a phase structure in which the total content of α phase and γ phase is 85% or more by area ratio and the content of γ phase is 25% or less by area ratio; and wherein the copper alloy casting has a mean grain size of 250 μm or less in a macrostructure at melt-solidification, and wherein the copper alloy casting has a shape determined by a mold.

10. A copper alloy casting containing:

Cu: 58 to 72.5 mass %; Zr: 0.0008 to 0.045 mass %; P: 0.01 to 0.25 mass %; one or more elements selected from Pb: 0.01 to 4 mass %, Bi: 0.01 to 3 mass %, Se: 0.03 to 1 mass %, and Te: 0.05 to 1.2 mass %; Sn: 0.05 to 4 mass % and/or Al: 0.01 to 4 mass %; As: 0.02 to 0.2 mass % and/or Sb: 0.02 to 0.2 mass %; one or more elements selected from Mn: 0.1 to 5 mass %, Si: 0.05 to 2 mass %, and Mg: 0.001 to 0.2 mass %; and Zn: a remainder, wherein the copper alloy casting satisfies the following equations, f1=[Cu]−3[P]+0.5([Pb]+[Bi]+[Se]+[Te])−0.5[Sn]−1.8[Al]−([As]+[Sb])+[Mn]−3.5[Si]−0.5[Mg]= 60 to 90, f2=[P]/[Zr]=0.5 to 120, f3=0.05[γ]+([Pb]+[Bi]+[Se]+[Te])=0.45 to 4, f4=[Zn]+2.5[Sn]+3[Al]=15 to 42, f5=([Zn]+2.5[Sn]+3[Al])/[Zr]=500 to 20000, and f6=([Zn]+2.5[Sn]+3[Al])/[P]=75 to 3000, wherein the content of each element 'a' is denoted as [a] mass %, the content of γ phase is denoted as [γ]% by area ratio, and each element 'a' that is not contained in the copper alloy casting is denoted as [a]=0;

wherein the copper alloy casting forms a phase structure in which the total content of α phase and γ phase is 85% or more by area ratio and the content of γ phase is 25% or less by area ratio; and wherein the copper alloy casting has a mean grain size of 250 μm or less in a macrostructure at melt-solidification, and wherein the copper alloy casting has a shape determined by a mold.

11. The copper alloy casting according to any one of claims 1 to 10, the copper alloy casting comprising Fe or Ni, or Fe and Ni as inevitable impurities, wherein when either Fe or Ni is included, the content thereof is restricted to be 0.2 mass % or less, and when both Fe and Ni are contained, the total content of Fe and Ni is restricted to be 0.25 mass % or less.

12. The copper alloy casting according to claim 11, wherein a two-dimensional shape of grains during melt-solidification is circular, substantially circular, oval, cross-like, acicular, or polygonal.

13. The copper alloy casting according to claim 11, wherein the copper alloy casting is a water contact metal fitting used continuously or temporarily in contact with water, or a structural material thereof.

14. A method of casting the copper alloy casting according to claim 11, wherein Zr contained to refine the grains is added during the casting process in a form of a copper based master alloy containing Zr, thereby preventing Zr from being added in a form of an oxide or a sulfide, or in the oxide and sulfide forms.

15. The copper alloy casting according to any one of claims 1 to 10, wherein a primary crystal is α phase during melt-solidification.

16. The copper alloy casting according to any one of claims 1 to 10, wherein a peritectic reaction occurs during melt-solidification.

17. The copper alloy casting according to claim 16,
wherein the copper alloy casting is a water contact metal fitting used continuously or temporarily in contact with water, or a structural material thereof.

18. A method of casting the copper alloy casting according to claim 16,
wherein Zr contained to refine the grains is added during the casting process in a form of a copper based master alloy containing Zr, thereby preventing Zr from being added in a form of an oxide or a sulfide, or in the oxide and sulfide forms.

19. The copper alloy casting according to any one of claims 1 to 10,
wherein a dendrite network is divided in a crystal structure during melt-solidification.

20. The copper alloy casting according to any one of claims 1 to 10,
wherein a two-dimensional shape of grains during melt-solidification is circular, substantially circular, oval, cross-like, acicular, or polygonal.

21. The copper alloy casting according to claim 20,
wherein the copper alloy casting is a water contact metal fitting used continuously or temporarily in contact with water, or a structural material thereof.

22. A method of casting the copper alloy casting according to claim 20,
wherein Zr contained to refine the grains is added during the casting process in a form of a copper based master alloy containing Zr, thereby preventing Zr from being added in a form of an oxide or a sulfide, or in the oxide and sulfide forms.

23. The copper alloy casting according to any one of claims 1 to 10,
wherein α phase is divided finely in a matrix, and γ phase or high Sn-concentrated area that is generated by segregation is distributed uniformly in the matrix.

24. The copper alloy casting according to any one of claims 1 to 10,
wherein, when the copper alloy casting contains Pb or Bi, Pb particles or Bi particles having a uniform diameter are distributed uniformly in the matrix.

25. The copper alloy casting according to any one of claims 1 to 10,
wherein the copper alloy casting is a water contact metal fitting used continuously or temporarily in contact with water, or a structural material thereof.

26. A method of casting the copper alloy casting according to claim 25,
wherein Zr contained to refine the grains is added during the casting process in a form of a copper based master alloy containing Zr, thereby preventing Zr from being added in a form of an oxide or a sulfide, or in the oxide and sulfide forms.

27. The copper alloy casting according to any one of claims 1 to 10,
wherein the copper alloy casting is a friction engaging member making a relative movement to a facing member continuously or temporarily in contact with the facing member, or a structural material thereof.

28. A method of casting the copper alloy casting according to claim 27,
wherein Zr contained to refine the grains is added during the casting process in a form of a copper based master alloy containing Zr, thereby preventing Zr from being added in a form of an oxide or a sulfide, or in the oxide and sulfide forms.

29. A method of casting the copper alloy casting according to any one of claims 1 to 10,
wherein Zr contained to refine the grains is added during the casting process in a form of a copper based master alloy containing Zr, thereby preventing Zr from being added in a form of an oxide or a sulfide, or in the oxide and sulfide forms.

30. The method of casting the copper alloy casting according to claim 29,
wherein the copper based master alloy containing Zr is a Cu—Zr alloy, a Cu—Zn—Zr alloy or an alloy further containing one or more elements selected from P, Mg, Al, Sn, Mn and B in addition to the said Cu—Zr alloy or Cu—Zn—Zr alloy.

* * * * *